(12) United States Patent
Huebner et al.

(10) Patent No.: US 8,192,434 B2
(45) Date of Patent: Jun. 5, 2012

(54) EXTERNAL FIXATION AND FOOT-SUPPORTING DEVICE

(76) Inventors: Randall J. Huebner, Portland, OR (US); Alexander Randall Shaevitz, Salem, OR (US); William McGrath, Colorado Springs, CO (US); Douglas N. Beaman, Hood River, OR (US)

( * ) Notice: Subject to any disclaimer, the term of this patent is extended or adjusted under 35 U.S.C. 154(b) by 258 days.

(21) Appl. No.: 12/432,956

(22) Filed: Apr. 30, 2009

(65) Prior Publication Data

US 2009/0275944 A1 Nov. 5, 2009

Related U.S. Application Data

(60) Provisional application No. 61/049,865, filed on May 2, 2008.

(51) Int. Cl.
*A61B 17/00* (2006.01)
(52) U.S. Cl. ............................................ 606/54; 602/23
(58) Field of Classification Search .............. 606/53–59; 602/23, 27–30, 62, 65–66
See application file for complete search history.

(56) References Cited

U.S. PATENT DOCUMENTS

| 1,863,188 | A |   | 6/1932  | Clash |           |
|-----------|---|---|---------|-------|-----------|
| 2,516,872 | A | * | 8/1950  | Hauser et al. | 602/27 |
| 4,338,927 | A | * | 7/1982  | Volkov et al. | 606/56 |
| 4,554,915 | A |   | 11/1985 | Brumfield |   |
| 4,771,768 | A |   | 9/1988  | Crispin |         |
| 4,998,935 | A |   | 3/1991  | Pennig |          |
| 5,031,607 | A | * | 7/1991  | Peters | 602/27 |
| 5,092,321 | A | * | 3/1992  | Spademan | 602/27 |
| 5,569,173 | A |   | 10/1996 | Varn |           |
| 5,913,841 | A | * | 6/1999  | Lamont | 602/65 |
| 5,997,537 | A |   | 12/1999 | Walulik |          |
| 6,155,998 | A | * | 12/2000 | Gilmour | 602/27 |
| 6,277,119 | B1 |  | 8/2001  | Walulik |         |
| 6,377,178 | B1 | * | 4/2002 | DeToro et al. | 340/573.1 |
| 6,613,049 | B2 |  | 9/2003  | Winquist et al. |  |
| 6,702,814 | B2 |  | 3/2004  | Walulik |          |
| 6,716,212 | B1 |  | 4/2004  | Pickens |          |
| 6,964,663 | B2 | * | 11/2005 | Grant et al. | 606/54 |
| 7,048,735 | B2 |  | 5/2006  | Ferrante et al. |  |
| 7,204,819 | B2 | * | 4/2007 | Berger | 602/26 |
| 7,306,601 | B2 |  | 12/2007 | McGrath et al. |  |
| 7,422,593 | B2 | * | 9/2008 | Cresina et al. | 606/54 |
| 7,597,674 | B2 | * | 10/2009 | Hu et al. | 602/23 |
| 7,749,224 | B2 | * | 7/2010 | Cresina et al. | 606/54 |
| 7,815,586 | B2 | * | 10/2010 | Grant et al. | 602/23 |
| 2006/0142682 | A1 | * | 6/2006 | Hassler et al. | 602/27 |
| 2007/0161984 | A1 | * | 7/2007 | Cresina et al. | 606/54 |
| 2008/0021451 | A1 | * | 1/2008 | Coull et al. | 606/54 |
| 2008/0051778 | A1 | * | 2/2008 | Surma et al. | 606/53 |
| 2008/0269741 | A1 | * | 10/2008 | Karidis | 606/56 |
| 2009/0131935 | A1 | * | 5/2009 | Yeager | 606/54 |

* cited by examiner

*Primary Examiner* — Eduardo C Robert
*Assistant Examiner* — Stuart S Bray
(74) *Attorney, Agent, or Firm* — Peter A Haas Esquire LLC

(57) ABSTRACT

In one preferred embodiment according to the present invention, an external fixation device for the foot and ankle of the human anatomical skeleton includes a yoke, three adjusters, and a base (or foot plate). The foot plate selectively couples to the yoke without the need of any tools, thereby enabling the patient to self attach and remove the foot plate from an existing circular fixation structure.

11 Claims, 17 Drawing Sheets

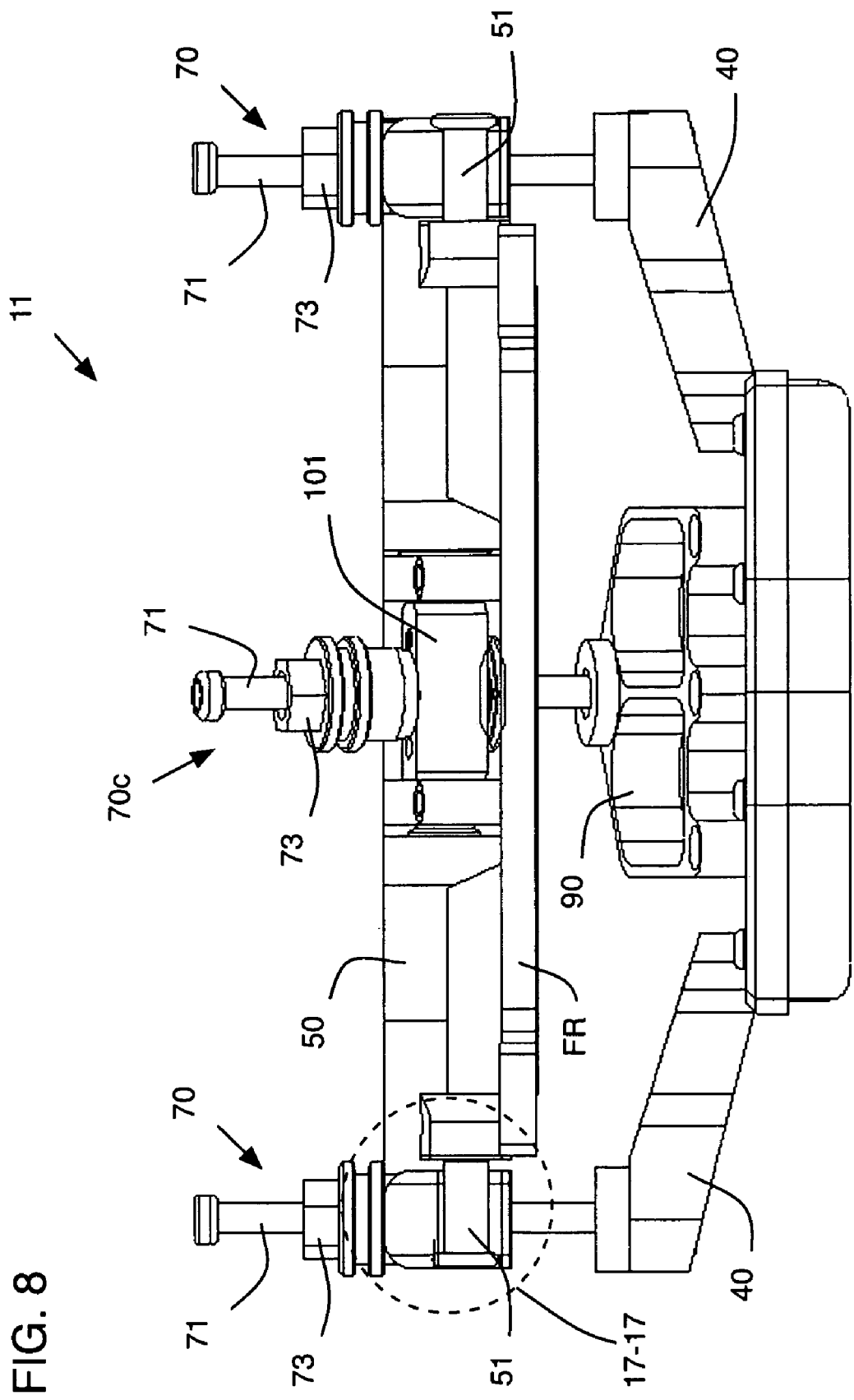

FIG. 18A
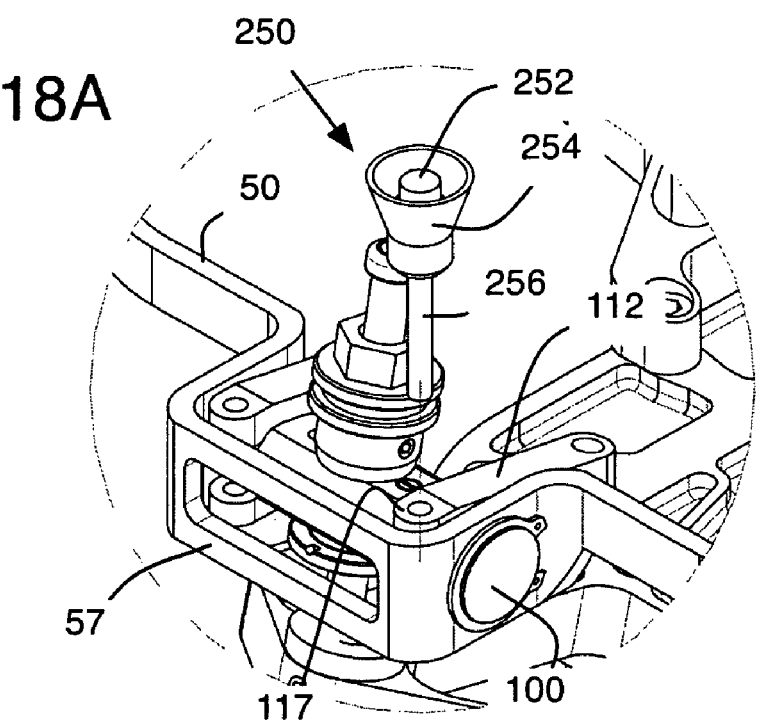
Detail A
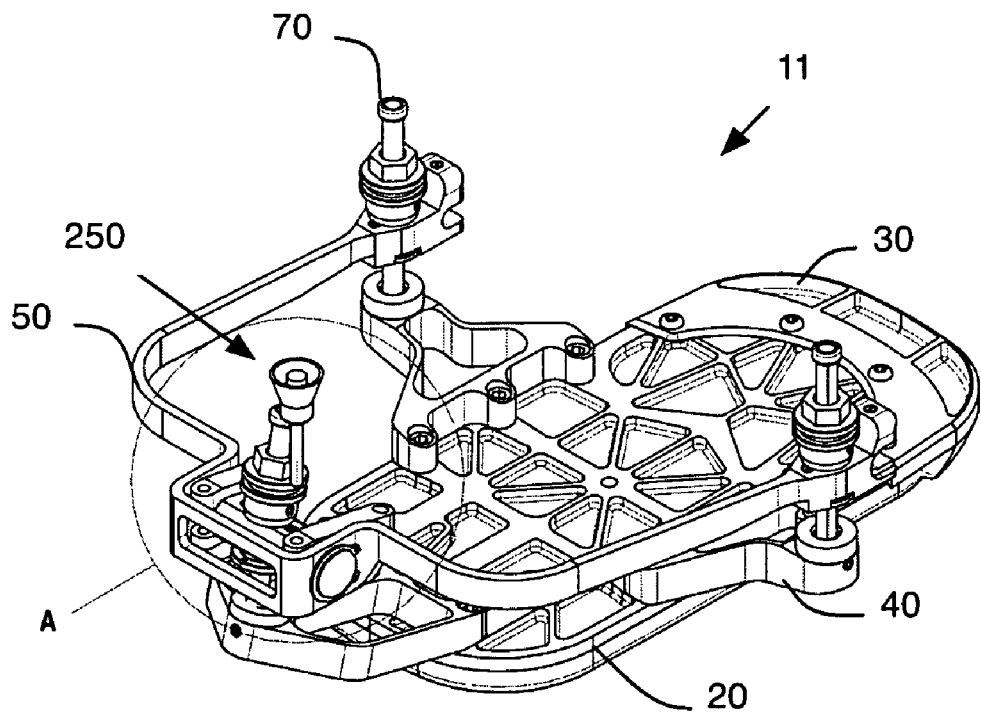
FIG. 18

EXTERNAL FIXATION AND FOOT-SUPPORTING DEVICE

PRIORITY CLAIM

The present application claims benefit under 35 USC Section 119(e) of U.S. Provisional Patent Application Ser. No. 61/049,865 filed on 2 May 2009. The present application is based on and claims priority from this application, the disclosure of which is hereby expressly incorporated herein by reference.

BACKGROUND

The present invention relates to therapeutic orthopedic devices for fixating, immobilizing, and manipulating the human anatomical skeleton, particularly the foot and lower leg. And, more specifically, the present invention relates to external frame systems and devices for fixating lower leg bones and the foot with respect to the tibia.

External Fixation devices locate segments of bone relative to a reference location of the skeleton for varied purposes including reconstruction of fractured or deformed extremities. By distracting or compressing portions of the anatomical skeleton, external fixation devices can correct angulation, rotation, and translation of targeted bones or bone segments.

External fixation—an orthopedic procedure utilizing external fixation devices—involves surgically securing bone pins both above and below a bone fracture or chosen site for manipulation, providing attachment points that may couple with or to another component, such as a clamp or frame member, of the external fixation system.

One particular form of external fixation, circular fixation (also called external ring fixation), is a proven medical treatment technique to overcome, correct, or repair many problems of the lower leg and foot stemming from traumatic injuries, infections, non-unions, or congenital abnormalities.

One drawback of circular fixation treatments includes a lengthy treatment duration—often in excess of one year—during which the patient's foot and lower leg are immobilized in a cumbersome external fixation structure consisting of varied components including pins, wires, support rods, clamps, and frames. This duration of immobilization is necessary for precise manipulation and to permit bone regrowth.

Another drawback of existing circular fixation treatments and systems is that patients have restricted movement. This restriction is a result of the quantity and placement of cumbersome components that—due to their size, weight, and anatomic placement—severely restrict and impair motion to a range that is far less than the patient's accustomed normal range.

Yet these components, despite their size and weight, are vital to ensure proper treatment. External fixation can practically manipulate bone in any desired combination of translation, rotation, angle, or length. When applied to the foot and lower leg, external fixation treatments include the use of structures incorporating one or more external ring frame members (semi-circumferential or full circumferential frame members) to encompass and stabilize the limb by pins and or tensioned wires. The circular frames are employed to capitalize on these biologic phenomenae that govern tissue (in particular, bone) growth under tension and optimized distraction rates.

Bone regrowth as a result of circular fixation applies an accepted treatment termed controlled distraction histogenesis, whereby bone is fractured and then slowly lengthened at a very specific and controlled rate to optimize bone regrowth.

As the fractured bone is distracted, new bone growth occurs in the fracture region and establishes a new segment of healthy bone in the defect. The tension that is created by gradual distraction stimulates the formation of new bone, skin, blood vessels, peripheral nerves, and muscle. Circular fixation thus allows for an external means of manipulating translational, rotational, angular, and even length discrepancies while preserving soft tissue from excessive trauma that would otherwise prevent early motion and use of the limb.

However, existing circular external fixation systems inadequately address the patient's desire and need to use the constricted limb as close to normal as possible. Specifically, existing external fixation systems inadequately address the patient's need for an ambulatory load-bearing construct that enables or approximates the patient's normal (unencumbered) gait. Existing solutions that attempt to address this patient need range from surgeon prescribed, makeshift devices to utilizing a second foot ring placed below the foot to provide rudimentary, albeit sub-optimal, support. Although these solutions provide a "contact" platform under the foot, they fail to provide adequate cushioning, adjustability [for gait], and removability, or any combination of these characteristics.

And, more problematic, injuries and other abnormalities of the foot require additional frame elements including a foot ring. A foot ring is mounted to the foot with pins and/or tensioned wires in the same manner as rings above the ankle are attached to the tibia. Foot rings can be difficult to align and mount either because of more challenging deformities of the foot such as equinus contractures or varus deformities, or simply because of the difficulty surgeons encounter when trying to manually align the foot ring properly with the foot. Often the result is an attached foot ring that is non-plantigrade, or poorly aligned with the horizontal axis of the foot. As a result, the patient often cannot load-bear due to hardware attachments beneath the foot ring, the position of the foot ring, the position of the foot ring relative to the foot, or because of a pre-existing anatomic position that prohibits them from walking normally.

In an attempt to provide adequate clearance for an inferior encumbrance, patients often have an additional ring, or footplate, attached beneath their foot that allows them to bear weight and, using crutches, ambulate. This additional ring or foot ring attaches with four (or more) threaded rods that are secured with multiple nuts above and below each ring. This requires both precise location in a clinical or surgical setting and tools including wenches.

Additionally, many prior-art foot rings, or foot-ring walking attachments, do not provide any cushioning or traction-enhancing features. So, in an attempt to provide patients with more comfort, some orthopedists have crudely attached materials with a walking, rubberized tread to the bottom of the additional foot ring. These devices represent existing elements of systems whose intended use(s) were for different locations but have been implemented as makeshift adaptations for this function.

Known prior-art or state-of-the-art external fixations systems present additional drawbacks when applied for use as a walking attachment. Frame members that were not designed specifically as a footplate do not provide for the cushion or tread necessary for such a longitudinal course of treatment. Moreover, these devices are difficult to adjust to a patient's comfort given the planar variances of each patient's foot position and the need for the device to adapt to a wide spectrum of variation between individual patients.

Further, because the adjustments made to existing devices require tools (such as wrenches), to tighten and loosen nuts on threaded rods and on bolts, it can be very difficult, if not impossible for a patient to accurately adjust their ring for comfort or hygiene. Any comfort gain by removal for bathing or at bedtime is eclipsed by the arduousness of this task and, often for the entire duration of treatment, an individual patient will not remove their load-bearing ring.

Normal ambulation is further encumbered by additional length due to the height of the external fixation systems. This additional length causes an abnormal gait and further causes hip and knee problems.

One device that recognizes the need for a walking platform is the "rocker bottom" attachment manufactured by DePuy, Johnson & Johnson. This device enables a direct attachment to the underside of the patient's foot ring, and provides a "rocker" type bottom that is intended to promote and ease the forward motion of a patient as they bring their limb forward, touch down, and then "rock" forward. The deficiency of this device is multifold in that it nearly eliminates all available attachment points for wire fixation to the foot ring due to it's size and shape that mirrors the foot ring and, hence eclipses, all attachment point options. The DePuy device, because it attaches using multiple bolts and nuts, makes very difficult if not impossible for the patient to remove his device when bathing or sleeping. Finally, and most significantly, the DePuy device does not inherently provide a means for planar adjustability; there is no available means for either a surgeon or patient to easily adjust the position of their means for comfort, supplemental correction, or just ambulating.

Of course, a curved bottom portion is generally known in the art to aid walking for patients in controlled motion devices. For example, Crispin, in U.S. Pat. No. 4,771,768 issued on 20 Sep. 1988, describes the benefits of a rigid shell with a curved bottom to provide a rocking heel to toe motion of a patient's foot during weight bearing when encumbered in a motion control cast.

Other external fixation devices for the repair of the anatomical skeleton are known. One state-of-the-art representative device, hereby incorporated by reference as if fully set forth herein, includes the external fixation system described by Walulik et al. in U.S. Pat. No. 6,277,119 issued on 21 Aug. 2001. The Walulik device includes interchangeable and distinct components that allow for a greater degree of surgeon flexibility in producing a desired construction to secure bone portions with bone pins. These components include at least one cylindrical support rod and a plurality of universal clamp assemblies for engagement with at least one support rod.

Specialized external fixation systems that enable a patient to bear weight on the fixed lower extremity are also generally known. Such specialized systems enable the gradual increase of the patient's own weight on the immobilized limb to hasten recovery and promote tissue and bone regeneration. One representative example of such specialized lower-extremity external fixation systems include the combination bone fixation/immobilization apparatus of Grant et al., described in U.S. Pat. No. 6,964,663 issued on 15 Nov. 2005 and this disclosure is hereby incorporated by reference as if fully set forth herein limb. The Grant device includes a walking attachment adapted to have a plurality of transfixation wires fixed thereto and includes a substantially rigid leg support assembly comprising a cuff and strap.

Problems common to the current-state-of-the-art devices, represented above, include an unacceptable level of precision that must be maintained during the creation of the frame structure in orientating each component while a multitude of fasteners are tightened. Further, as many of the components interact with other components, manipulation or adjustment of one selected clamp, for instance, requires cooperating adjustments to several sub-systems and fasteners. Not only is such adjustments time-consuming, they are often impossible for the patient to make on their own because the patient is unable to reach the fasteners due to poor flexibility or simply because the location is out of the range of normal-human motion for a device worn on the foot. Moreover, the interdependent nature of the fasteners often require incremental adjustments made in sequence with each of the multiple fasteners, which requires a skill beyond the average patient.

Attempts to make external fixation systems more quickly and easily assembled and adjusted include the adjustable bone stabilizing frame system described by Wainquist et al. in U.S. Pat. No. 6,613,049 issued on 2 Sep. 2003. The Wainquist device includes clamping members with friction pins internally mounted in each clamp, which engages a rod-member once the rod is inserted into the jaws of the clamp.

Another external fixation system, described by Ferrante et al. in U.S. Pat. No. 7,048,735 issued on 23 May 2006 includes clamping elements that provide three-axes of rotation relative to the other capture member.

Despite the varied attempts at improving external frame fixation systems, many problems specific to the lower extremity and, particularly, to the foot, have not been adequately addressed. For example, patient comfort, gait, hygiene, ease of removal are inferior in known systems. Further, self adjustability by the patient, providing a flexing suspension to absorb shock from gait, providing a more normalized gait, reducing complexity, making a system more economical to produce, and reducing the number of components are all characteristics yet to be incorporated in known external frame fixation systems. Thus, there remains a need for an improved external ring fixation system particularly adapted for use with the foot that overcomes these aforementioned limitations.

SUMMARY OF THE INVENTION

The present invention overcomes the problems of the current state-of-the-art in external fixation systems. In a preferred embodiment, the present invention provides an external fixation system that improves patient comfort, enables a more normalized gait, encourages good hygiene, and provides ease of removal. Further, a preferred embodiment of the present invention provides mechanical features that enable self adjustability by the patient, provide a flexing suspension to absorb shock during gait, enable a more normalized gait, reduces complexity, is more economical to produce, and reduces the number of components compared to contemporary systems.

In one preferred embodiment, the present invention includes a system and device for external fixation of the anatomical skeleton, particularly as it relates to the lower leg, ankle, and foot. In this embodiment, patients undergoing ring external fixation treatment of foot and ankle problems have increased ambulation and function over any known or current systems and devices. The device of this embodiment is specifically made to attach to a (155 mm) Taylor Spatial Frame brand foot ring available from Smith & Nephew, Memphis, Tenn., USA, for patients undergoing treatment of pathology of the lower extremity requiring fixation of their foot in the ring external fixator. The device of the present invention fully adjusts allowing patients to ambulate with as normal a gait as possible with the ring fixator in place. The device's adjustability allows for deformity of the foot and ankle as well as non-plantigrade mounting of a foot ring, which may occur with foot ring applications. The device includes quick connect and release mechanisms that allow patients to self remove the walking portion of the device.

In one preferred embodiment, the system of the present invention includes an external ring fixation device consisting of three clamps commonly applied to the walking portion consists of an aluminum plate with a rubberized, surface-contacting sole or, alternatively, a rocker-sole addition. The plate is connected to the three specialized clamps via adjusters, a unique assembly consisting of an adjustable rod (or strut) and ball-and-socket joints. This allows adjustability, stability, and strength.

In this preferred embodiment, the external ring fixation device provides tremendous improvement in patient acceptance and ability to tolerate the external fixation device, comfort and functionality; allowing them to walk with a more normalized gait pattern by being able to precisely adjust the way their limb strikes the ground during ambulation. As it is easily removable without the need for any tools, patients can self-remove for hygienic purposes and re-apply the device without needing the assistance of trained medical personal in a clinical setting. Also, the device adjusts easily by hand and thus the patient may adjust the device for a more comfortable fit. This self-adjustability feature of the present invention influences patient tolerance and recovery as it enables the patient or surgeon to control both ideal foot position as well as the extent of negative, partial, or full weight transference.

The ability to influence motor sensory either through the removal of the entire device, thereby permitting full plantar contact of the foot with the ground, or through the patient's or surgeon's newfound ability to control, incrementally, the percentage of the patient's load permitted to contact the device surface. This affords a unique feature that has not existed with previous devices due to the inherent arduousness of changing height or angulation with a wrench and multiple nuts, and because the absence of any measurement calibrations in previous devices made it nearly impossible to record, with precision, quantitative changes. The present device permits both easy adjustments and strut calibrations to permit the tracking and creation of a patient foot position history.

The collection of post-operative data that is allowed by the device's calibrated struts—allows a surgeon to determine and prescribe activity levels that are aggressively, or less vigorously based on variables such as patient weight, foot position, and health. Because of the ease of adjustability and measurements on the struts, the patient can adhere to a surgeon's prescription for foot position and weight transference. Also, the device allows for a patient to provide less subjective, and more quantitatively based feedback to the surgeon regarding pain, or motor sensation, as correlates to specific, recordable strut measurements.

Another feature of the present invention is the patient can approach a range of motion that is closer to a normal gait and provides a greater range of motion for the patient when compared to prior-art attempts. And, by achieving a more normal gait pattern, the potential for pin site loosening of half-pins in the tibia (a problem common in many prior-art devices) may be substantially lower; thus negating the need for costly frame modifications performed in the operating room and reduces pin-site infections, which are commonly seen in patients with Foot-mount external ring fixation systems.

Early tests suggest the additional likely benefits of the present invention due to a more normalized gait-pattern include a reduction in the stress placed on the tibial rings and tibial fixation structures and couplings. Over time, stress on the tibial rings and related fixations structures can loosen fixation and, if left unattended, cause harm to the patient, promote infection, and require visits to the clinic, and—in certain instances—additional surgical procedures, all of which add extra cost and risk to the patient.

Finally, the various preferred embodiments of the present invention enable patients with improved mobility, comfort, and adjustability by use of various combinations of elements described herein. These improvements, compared to the devices of the prior art, provide—among other benefits—improved sensory feedback necessary for a more speedy recovery.

A external fixation device for attachment to a lower-extremity external fixation frame for a patient, the external fixation device comprising:
a base adapted to contact a surface during walking; and
a plurality of medial-lateral supports coupled to the base at a first end and each medial-lateral support having a yoke and bracket assembly coupled to an oppositely disposed second end wherein the associated yoke releasably and selectively couples to the lower-extremity external fixation frame.

The external fixation device wherein the plurality of medial-lateral supports comprises three medial-lateral supports.

The external fixation device wherein the plurality of medial-lateral supports further comprises: a means for pivotably coupling the medial-lateral support to the base at the first end and means for fixably coupling the medial-lateral support to the yoke at the second end.

The external fixation device wherein each of the plurality of medial-lateral supports cooperates with each other medial-lateral support and each medial-lateral support further comprises: a yoke cooperating with bracket to enable medial and lateral adjustments of the external fixation device.

The external fixation device further comprising an air bladder coupled to a first face of the external fixation device and adapted for selective volumetric changes by pumping or releasing air into a bladder-chamber by a means for pumping whereby a patient may adjust the volume to better suit the patient's comfort when the external fixation device is coupled to the lower extremity.

A mobility-enhancing external frame fixation device for the foot and adapted for use with a lower extremity external frame fixation system, the device comprising: a base plate for selectively supporting the foot at varying levels of weight-bearing in accordance with known external fixation techniques; a first and second lateral bracket coupled to opposing lateral sides of the base plate and adapted to receive a corresponding first and second medial-lateral adjuster; a posterior bracket coupled to the base plate and adapted to receive a corresponding third medial-lateral adjuster, a posterior pivot coupled to the third medial-lateral adjuster; and a yoke coupling to the first, second, and third medial-lateral adjusters.

An alignment rod for a lower-extremity external fixation frame, the alignment rod comprising: a base for providing support means for a vertically arranged alignment guide pin, the alignment guide-pin adapted for visual alignment of an external fixation system with the axis of the tibia; an external fixation device-insertion pin coupled to the base on a face opposite from and off-axis with the vertically arranged alignment guide pin, the external fixation device-insertion pin adapted to selectively engage a corresponding feature on the external fixation frame, the vertical axis of the external fixation device-insertion pin being generally parallel to the vertical axis of the alignment guide pin.

An alignment rod adapted to enable adjustment of an external frame fixation system having a external fixation device, a first and second medial-lateral strut and a posterior strut according to the present invention.

An external fixation frame having a external fixation device, the external fixation device comprising: a first medial-lateral bracket and corresponding first yoke; and a second medial-lateral bracket and corresponding second yoke, whereby the first yoke cooperates with the first bracket to enable pivoting of the yoke relative to the bracket and the second yoke and bracket fixably couple so prevent pivoting; and the pair of first and second medial-lateral bracket and yoke combinations further cooperate to enable adjustment of the external fixation device relative to the fixation frame.

An external fixation device for attachment to an external fixation frame, the external fixation device comprising: a base adapted to contact the ground during walking; three or more medial-lateral adjusters coupled to the base and adapted to enable the base to couple to at least one yoke and bracket assembly, the yoke and bracket assembly being adapted to enable removable fixation of the external fixation device to the external fixation frame.

The external fixation device wherein at least one medial-lateral adjuster further comprises: a means for pivoting the medial-lateral adjuster at a first end; and a second end disposed opposite from the first end, the second end adapted to fixably couple to the yoke.

The external fixation device wherein the at least one yoke comprises: a posterior yoke adapted to pivot around a posterior attachment.

The external fixation device wherein one of the three or more medial-lateral adjusters comprises: a posterior medial-lateral adjuster having a first end, the first end adapted to pivot in all planes, and the posterior medial-lateral adjuster further comprising a second end disposed opposite the first end, the second end adapted to pivot about one plane.

The external fixation device wherein the three or more medial-lateral adjusters further comprise: means for enabling each medial-lateral adjuster to pivot at the base.

The external fixation device wherein the three or more medial-lateral adjusters further comprise: a first medial-lateral adjuster, a second medial-lateral adjuster, and a posterior medial-lateral adjuster, wherein each medial-lateral adjuster is adapted to enable pivotable rotation at the base around an x, y, and z axis at a base-end of the corresponding medial-lateral adjuster; and wherein the first medial-lateral adjuster and second medial-lateral adjuster, at a respective yoke-end disposed opposite the base-end of the corresponding medial-lateral adjuster are fixably coupled to a corresponding yoke; and the posterior medial-lateral adjuster is adapted to pivot around one axis at a corresponding yoke-end, the yoke-end being disposed opposite the base-end.

The external fixation device wherein the three or more medial-lateral adjusters further comprise: a threaded end to enable adjustments between the yoke and the base.

The external fixation device further comprising: an extension piece adapted to coupled to an anterior end of the base, whereby the extension piece enables the base to extend to fit differing foot sizes.

The external fixation device wherein the yoke further comprises: a receiving through-hole adapted to receive a selectively removable pin, whereby the pin enables the yoke to be coupled to the external fixation device.

A method for externally fixating a lower extremity, the method comprising: providing an external fixation frame having a plurality of mounting brackets; providing a external fixation device assembly adapted to removably couple to the external fixation frame; providing at least one medial-lateral adjuster having adjustments in multiple planes; and providing a yoke adapted to engage the medial-lateral adjuster.

DRAWING

FIG. 8 is a front view of the embodiment of FIG. 6.

FIG. 18 is an off-set rear-view of another embodiment of the present invention and illustrates the locking pin attaching means.

FIG. 18A is detail "A" of FIG. 18.

DESCRIPTION OF THE INVENTION

Figure 1:
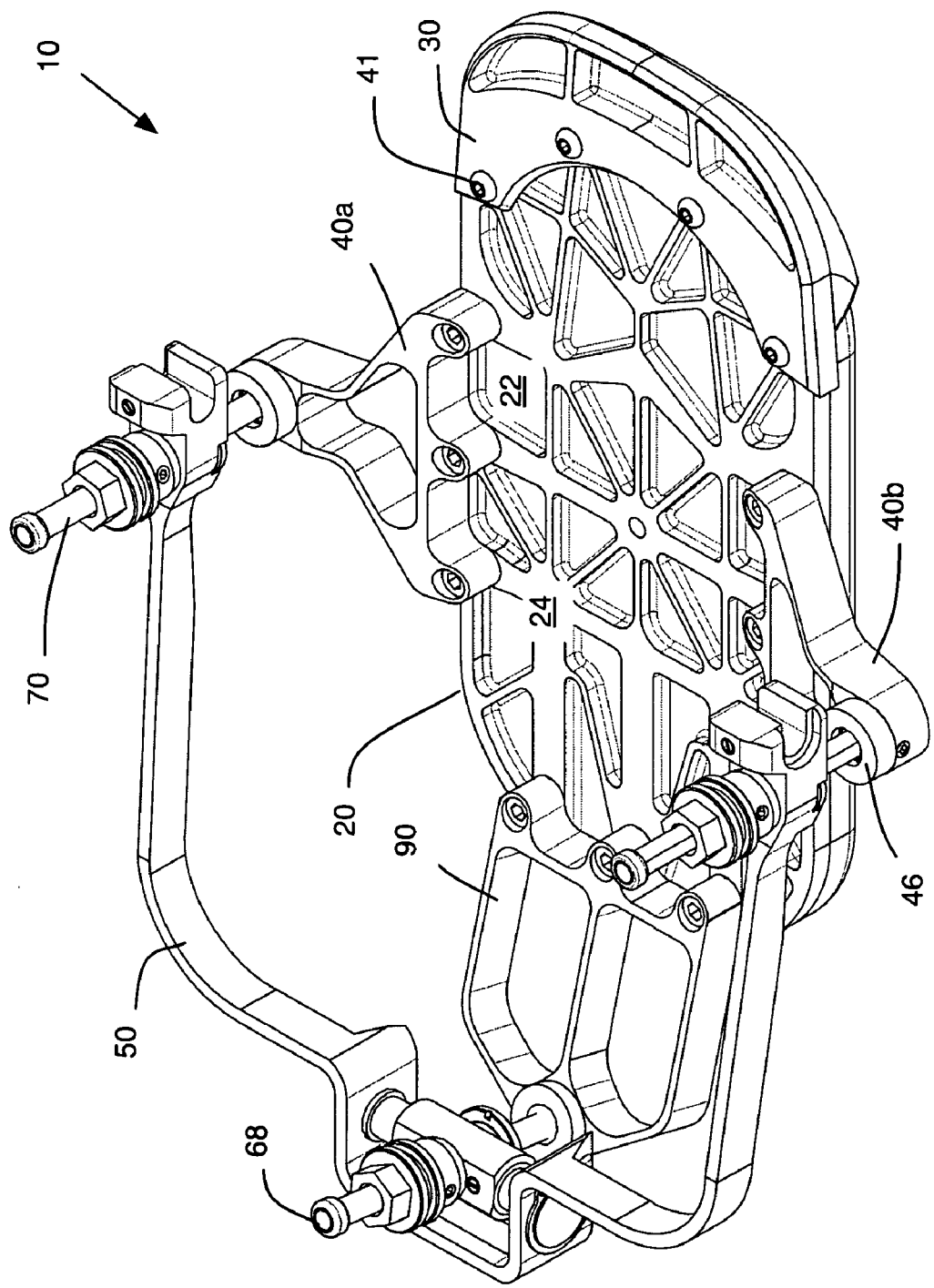
FIG. 1 is an offset, left-side perspective view of a first preferred embodiment of the present invention.

Possible embodiments will now be described with reference to the drawings and those skilled in the art will understand that alternative configurations and combinations of components may be substituted without subtracting from the invention. Also, in some figures certain components are omitted to more clearly illustrate the invention. In the prior-art, the term "foot-ring" and "foot-plate" often are used synonymously. However, in the present invention an attempt is made to distinguish the known prior art device that surrounds the foot (foot ring) from the present invention that includes components that couple to this foot ring and components adapted for use by the plantar surface of the foot. The later type components are termed foot-plates, or as used herein, a base plate.

FIGS. 1-4 illustrate a first preferred embodiment of the present invention and provide an overview contextualizing the various components. In this embodiment, a FRAME-WALKER™ brand (available from Quantum Medical Systems, LLC of Portland, Oreg., USA) external fixation device 10 for the foot of the anatomical skeleton includes a yoke 50, three adjusters 70 (two medial-lateral 70a 70b and one posterior 70c), a posterior bracket 90, a posterior pivot 100, a pair of lateral brackets 40a and 40b (or generally bracket 40), a base plate 20 (also referred to as a foot-plate), and a toe-piece extension 30. The device 10 adapts to selectively and releasably couple to existing ring fixation systems such as a Smith & Nephew, Taylor Spatial Frame Foot Ring, as would be well-understood by those having ordinary skill in this art.

In the first preferred embodiment illustrated in FIGS. 1-4, the present invention includes a mobility-enhancing external frame fixation device 10 for the foot adapted for use with a lower extremity external frame fixation system for immobilizing and fixating the anatomical skeleton. The device comprises a base plate 20 for selectively supporting the foot at varying levels of weight bearing in accordance with known external fixation treatment procedures, methods, and techniques.

Accordingly, this first preferred embodiment contemplates an external fixation device 10 for attachment to a lower-extremity external fixation frame 14 (of FIG. 6, for example) for a patient. The device 10 of FIGS. 1-4, for example, comprises a base plate 20 adapted to contact a surface during walking. The base plate, a generally co-planer and rectilinear flat plate, includes rounded corners and an overall thickness.

Figure 2:
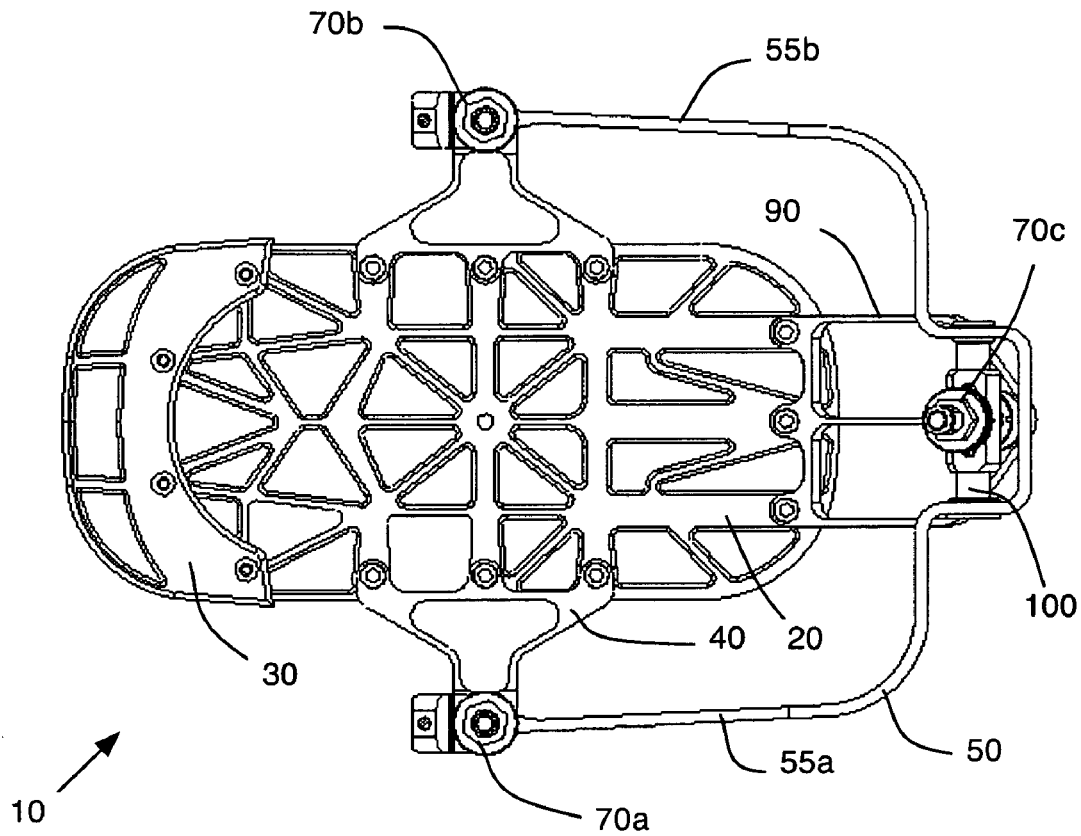
FIG. 2 is a top view of the embodiment of FIG. 1.
Figure 3:
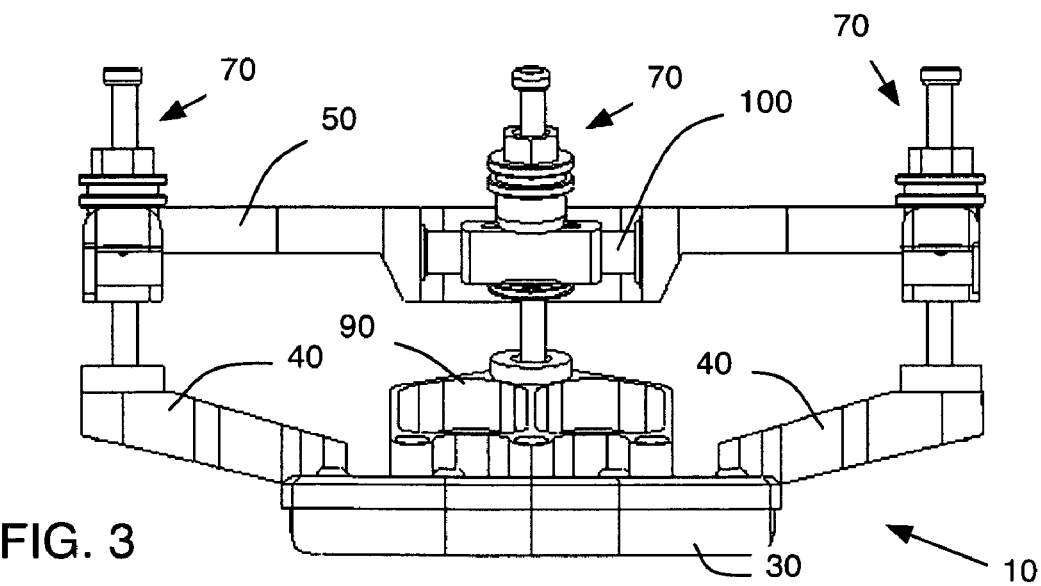
FIG. 3 is a front view of the embodiment of FIG. 1.

To reduce weight and yet ensure a suitably stiff plate member, the base plate includes a solid base panel 22 of a thickness less than the overall thickness of the base plate, and truss-like members 24 arranged to provide adequate stiffness to the base plate for its intended purpose, yet present light-weight to enhance patient safety and comfort. FIGS. 1 and 2 illustrate a preferred pattern of the truss-like members 24 and solid panel 22. However, other contemplated embodiments include the absence of a solid panel and, therefore, only the truss-like members would remain. And, of course, other patters of material would work as well including a solid panel, or other patterns of alternating thicknesses or webs, as would be well-appreciated by those of ordinary skill in this art.

Figure 4:
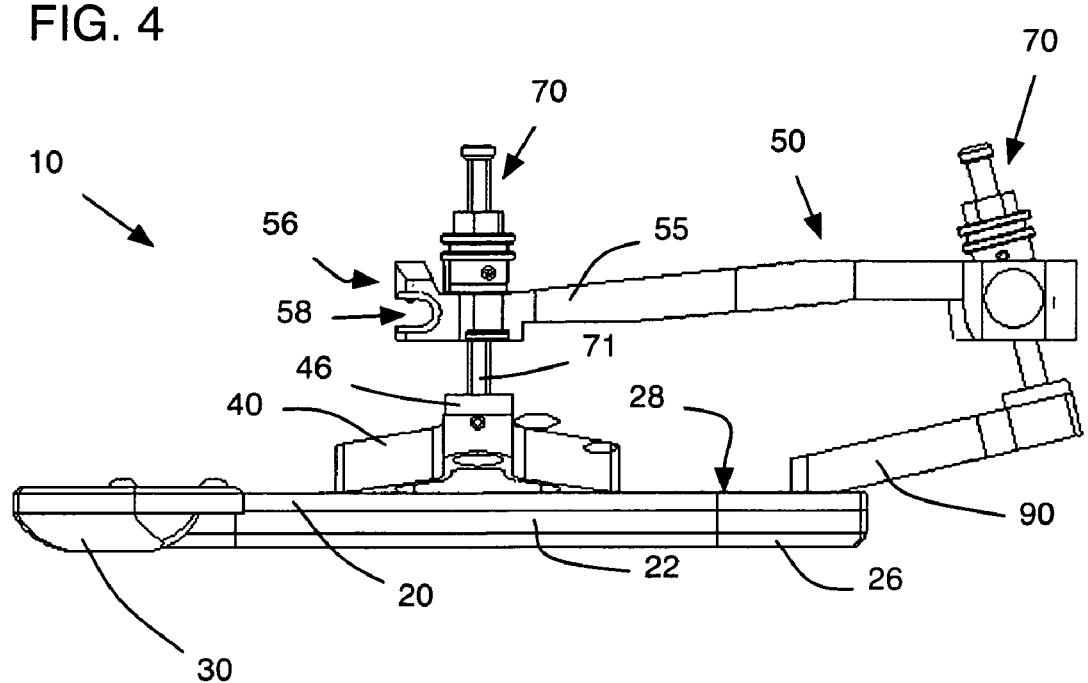
FIG. 4 is a right-side view of the embodiment of FIG. 1.
Figure 9:
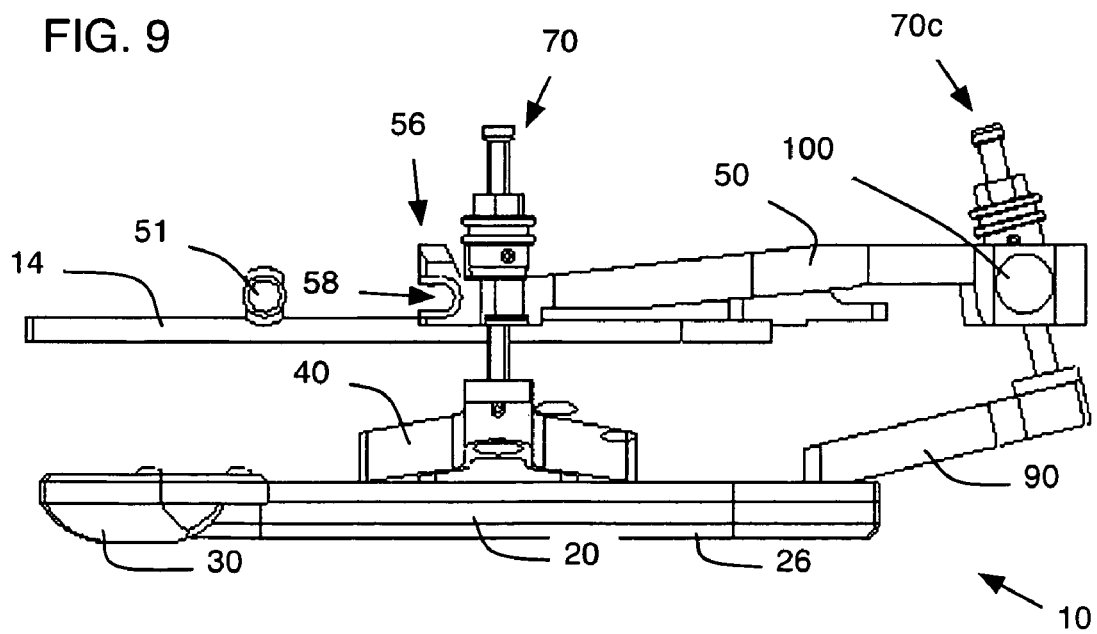
FIG. 9 is right side view of the embodiment of FIG. 6.

On a bottom surface of the base plate (opposite the top surface 28), a traction surface 26, such as a rubberized, or rubber-like synthetic gripping member 26 adheres, as FIG. 4 illustrates. This traction-enhancing material is coupled to the bottom surface of the base plate by means well understood in the art, and includes, an epoxy-like adhesive for a bond of the traction surface to the base plate. The traction-enhancing surface, such as rubber or a similar synthetic may be adhered or otherwise coupled to the bottom surfaces of the foot-plate (base plate 20) to provide enhanced comfort, safety, and traction. One suitable contemplated traction-enhancing surface that enables the base plate to adapt for contacting a surface includes an EVA (ethyl-vinyl-acetate) material having the trade name Vibram available from Quabaug Corp. of 18 School Street, North Brookfield, Mass. 01535, USA. And this material adheres to the underside of the base plate by known adhesives and methods of using those adhesives as would be well understood in the relevant art.

The base plate further includes mounting holes, either threaded or through-holes, as would be understood in the art and are adapted to receive fasteners or other components as further discussed herein. The base plate 20 further includes a length and a width appropriately sized for the patient's foot.

To reduce complexity and cost, a standardized set of base plates, or a single-sized base plate, can readily be determined to fit a maximum number of different sized patient's feet. An extension plate, such as a toe extender 30, can selectively couple to the base plate if additional length is needed for a particular patient. Most adults will fit the base plate in its standard width. Those with wider or those with substantially smaller (for example, children) feet can be fitted with scaled-up or -down versions of this preferred embodiment without departing from the scope, functionality, and intent of this first preferred embodiment.

Figure 13:
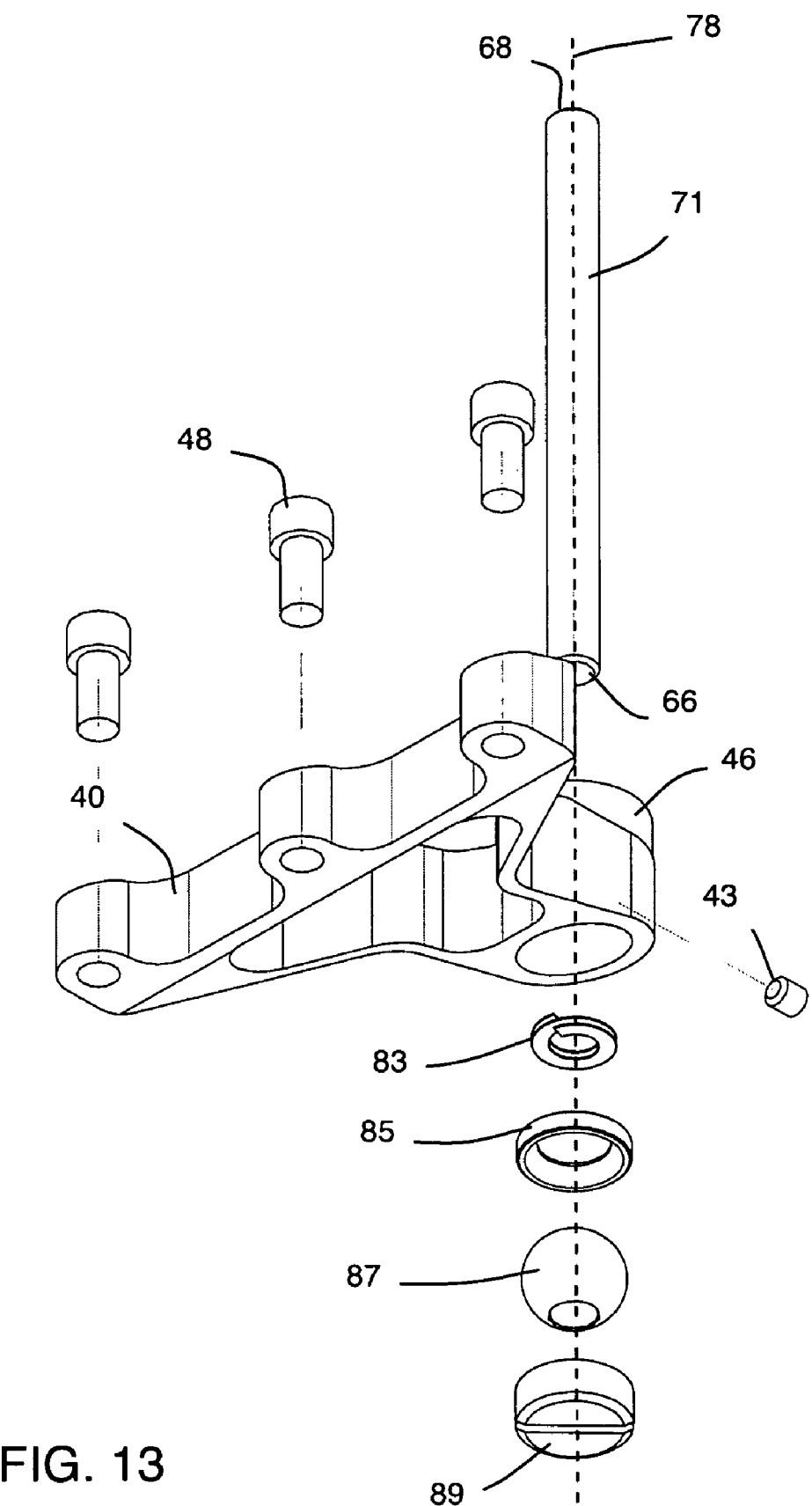
FIG. 13 is an exploded view of other components of the device according to a preferred embodiment of the present invention.
Figure 14:
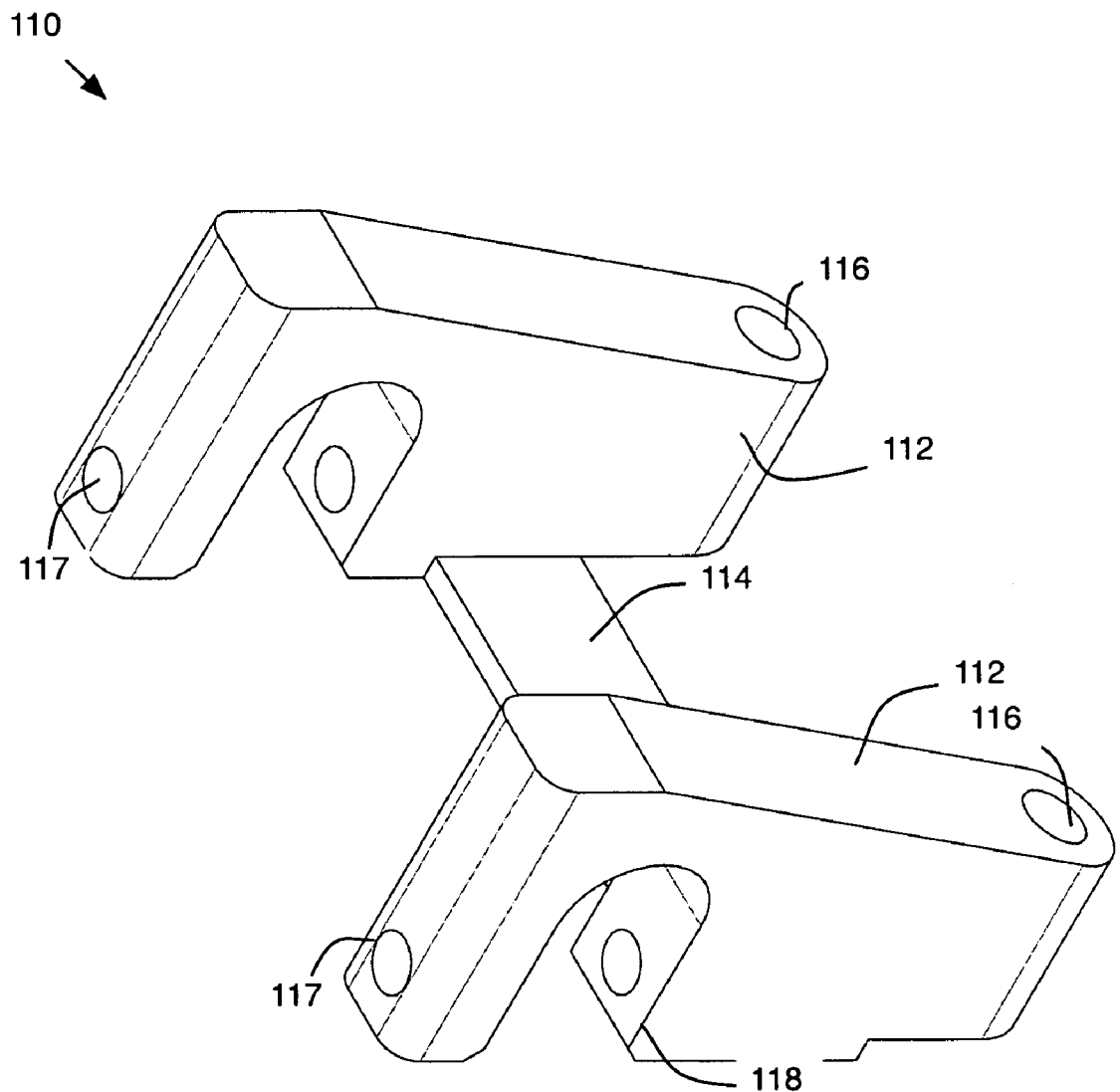
FIG. 14 is an alternative posterior block according to one embodiment of the present invention.

In alternative embodiments, the base plate includes a at least one bracket 40, or preferably a first medial-lateral bracket 40*a* coupled to a first (right) side of the base plate by a set of fasteners 48 (as FIG. 13 shows, for example) and a second medial-lateral bracket 40*b* similarly coupled to the opposite (left) side of the base plate 20 and a third, posterior bracket 90 coupled to the back of the base plate. Each respective bracket adapts to couple to the at least one associated adjuster 70, the bracket further comprising a shoulder 46 adapted to receive the first end 66 of the support strut 71. The shoulder 46 further adapts to prevent longitudinal movement of the support strut 71 relative to the base plate by means of the strut assembly including cap screw 89, ball joint 87, bushing 85, lock washer 83 and fastener 43, as described herein. The shoulder 46 further cooperates with the support strut first end 66 to enable the support strut 71 to pivot 360-degrees about the longitudinal axis 78.

Each bracket 40*a*, 40*b*, and 90 may couple to the base plate, or alternatively, be formed as part of the base plate (by casting, low pressuring, casting, machining from a solid block, or other methods). The brackets, further, include features that provide strength and rigidity for mounting the associated adjuster, but also should be as light as possible for patient comfort and recovery. Accordingly, the brackets include webbed trusses for strength and associated voids to reduce weight, as the Figures clearly show.

This first preferred embodiment further comprises at least one adjuster 70 coupled to the base plate 20 by known fastening means including recessed-head set screws or other similar fasteners. In a second preferred embodiment there are exactly three adjusters 70. Each first 70*a*, second 70*b*, and third 70*c* adjusters couple to the base plate a corresponding first, second and third position. For example, the set of adjusters 70 consists of two, oppositely positioned medial-lateral adjusters on, respectively, the left and right side of the base plate 20, and a third, or posterior adjuster located on the back of the base plate.

Figure 11:
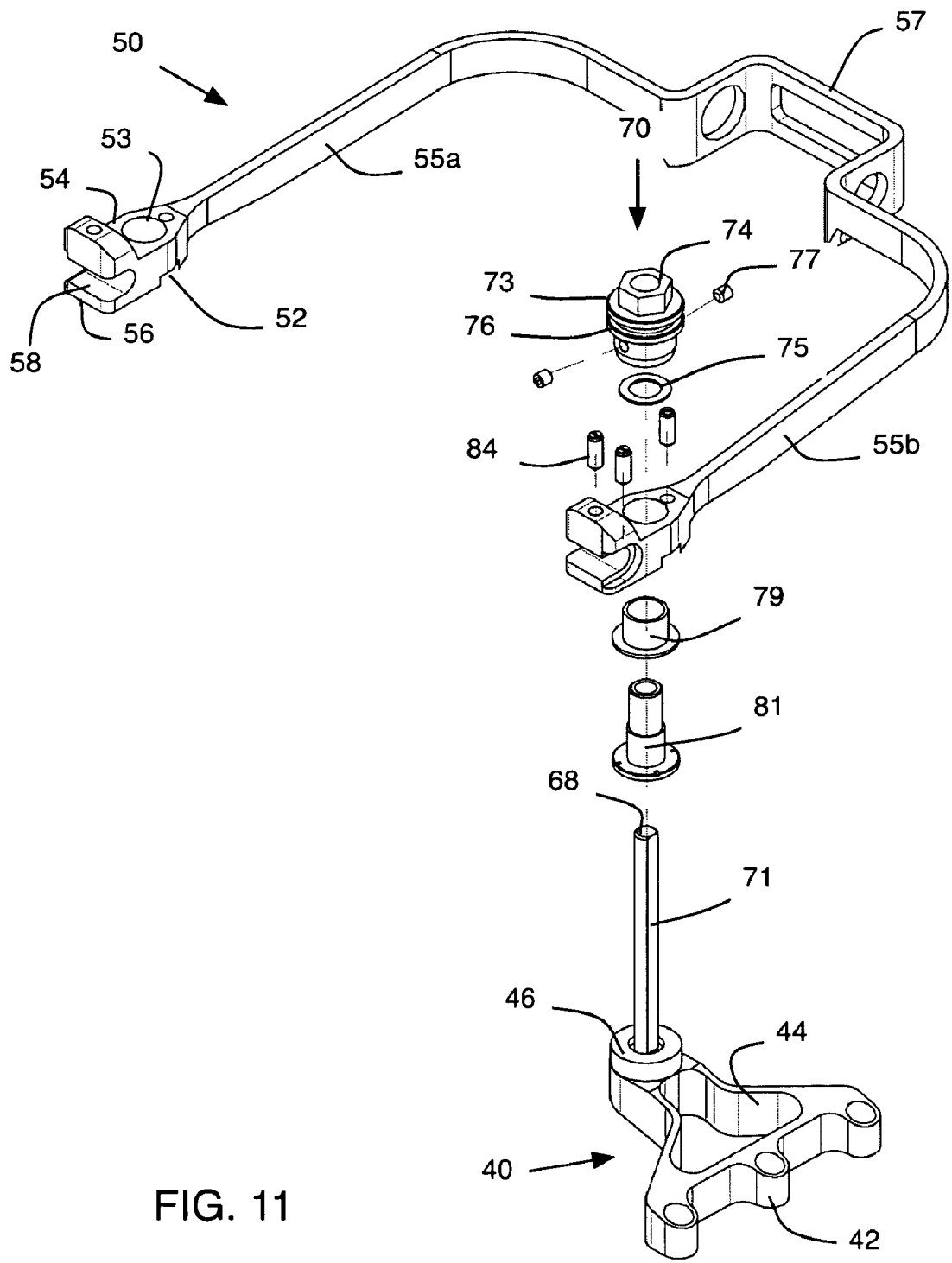
FIG. 11 is an exploded view of a certain components of the device according to a preferred embodiment of the present invention.

Because each adjuster in this first preferred embodiment comprises similar elements, only one adjuster 70 will be described in detail. FIGS. 11 and 13 detail a representative adjuster 70. Accordingly, the at least one adjuster 70 comprises a support strut 71 having a longitudinal axis 78 defined between a first end 66 and a second, opposite end 68 with an intermediate portion (the various figures do not provide a reference number for this intermediate portion—it being understood by those skilled in the art that a strut having two opposite ends necessarily has an intermediate portion linking those two ends) disposed between the first and second ends. The strut first end 66 adapts to insert into a ball joint 87, which is likewise adapted to receive the first end of the strut so when coupled together the strut is operable and adapted to enable 360-degrees of rotation of the strut about the longitudinal axis. Moreover, this combination of strut and ball joint sits in a mating feature provided by a bracket 40 on the base plate 20, and this function and corresponding elements are further described, below. Further, the strut intermediate portion, or preferably, the entire length along the longitudinal axis 78 comprises a threaded surface (this feature is not depicted in the figures). The threaded body of the strut 71 enables a mating element to selectively and adjustably position on the strut—thus the relative height of the mating element can be adjusted relative to the base plate, yet the strut can rotate about 360-degrees at the same time, the importance of this rotation and fixed vertical height of the strut will become apparent in the subsequent disclosure herein.

This first preferred embodiment further includes a yoke 50 adapted to couple to the at least one adjuster 70 and the yoke further adapted to selectively and releasably couple to the external fixation frame. The yoke 50 is described in further detail, below.

This first preferred embodiment further includes the base plate 20 having a bracket 40 or, alternatively, a feature integrated in the plate, this feature. Importantly, the shoulder 46 (for example, as FIGS. 1 and 13 show) adapts to receive the ball joint 87 of the at least one adjuster 70. This enables the strut 71 of the adjuster 70 to pivotably couple to the base plate (either directly or via bracket 40, which carries the shoulder 46 to a desired position offset from the plane of the base plate and off axis from the corresponding left, right, or back edge of the base plate, as FIGS. 1-4 illustrate) to enable the strut to rotate 360-degrees about the strut longitudinal axis, the longitudinal axis being generally perpendicular to a plane defined by the base plate. As would be appreciated by those skilled in the art, the strut and ball assembly are retained in position to prevent vertical travel of the assembly when in the shoulder. Accordingly, a cap screw 89 mates with a corresponding feature on the bottom portion of the shoulder and a bushing 85 and lock washer 83 sit atop the ball joint 87 and this assembly, moreover, is fixed in position by a fastener 43, as FIG. 11, and exploded assembly view, illustrates. In this manner the strut cannot move up or down (vertically) relative to the base plate, but can rotate about its own longitudinal axis.

The strut assembly 70 further includes a cap (not shown in the figure) located at the second end, the cap prevents over adjustment or inadvertent dis-assembly of the various components of the strut. Referring particularly to FIG. 11, as the strut adapts to slideably fit through the yoke (described below), the strut includes a bushing 79, a washer 75, and an adjustment knob 73. The adjustment knob assembly 73 adapted to selectively position and rotatably couple on the intermediate portion of the strut whereby rotation in a first direction causes the yoke to move in a corresponding first direction along the strut longitudinal axis and rotation in a second, opposite direction causes the yoke to move in a corresponding second direction along the strut longitudinal axis. Accordingly, the adjustment knob includes a mating internal treaded, through-hole body member adapted to engage a corresponding feature on the threaded strut 71.

As particularly detailed in FIG. 11, the adapter 70 includes an adjustment knob 43 having a hexagonal head 74, which can receive a standard or metric wrench. But, in use, the adjustment knob can easily be turned by hand by means of circumferencially arranged gripping bars 76. Further, to assist a more precise location of the yoke 50 (and thereby affecting the pitch and angulation of the plate 14), the strut 70 includes measured or scaled markings (either a relative scale or an actual measurement such as milli-meters, for example).

Additionally, by means of at least one spring-loaded ball plunger 84, for example two oppositely place plungers that cooperate with a detent feature on threaded sleeve 81. The spring-loaded ball plungers have an exterior threaded surface adapted to mesh with a corresponding interior threaded hole on the wrist 54 of the yoke 50.

Detents are included on threaded sleeve 81 for each quarter turn and as the adjustment knob is turned, each quarter-turn will result in a vibration when the spring-loaded ball expands into the detent on threaded sleeve 81. The knob attaches to threaded sleeve 81 by means of two small set screws 77. In turn, threaded sleeve 81 threads to the strut 71. Thus as the knob turns, and since the strut is fixed vertically, the knob travels up or down (depending on direction of the rotation on the knob) and carrying or pushing the yoke arm accordingly.

In this first preferred embodiment, as best illustrated by FIG. 11 and FIGS. 1-4, for example, the yoke 50 further comprises a generally U-shaped body having a first-yoke arm 55*a* and a second-yoke arm 55*b*, each respective yoke arm comprising a wrist 54 feature adapted to enable the strut to pass through a center opening 53 defined by the wrist. In this opening, a bushing 79 disposes and adapts to provide some resistance to the strut but still enable slidable engagement and rotation and pivoting of the strut 71.

The yoke first arm 55*a* and yoke-second arm 55*b* each respectively further comprise an upper and lower support member 56 defining a generally c-shaped fulcrum rest 58 and a spring-loaded ball plunger (similar to item 84 described herein) arranged perpendicular to the generally c-shaped fulcrum rest, thus enabling the respective first and second yoke arms to selectively couple to the frame 14. Joining the first and second arms, the yoke further includes a pivot cradle 57 disposed intermediate to the first 55*a* and second 55*b* yoke arms.

Figure 6:
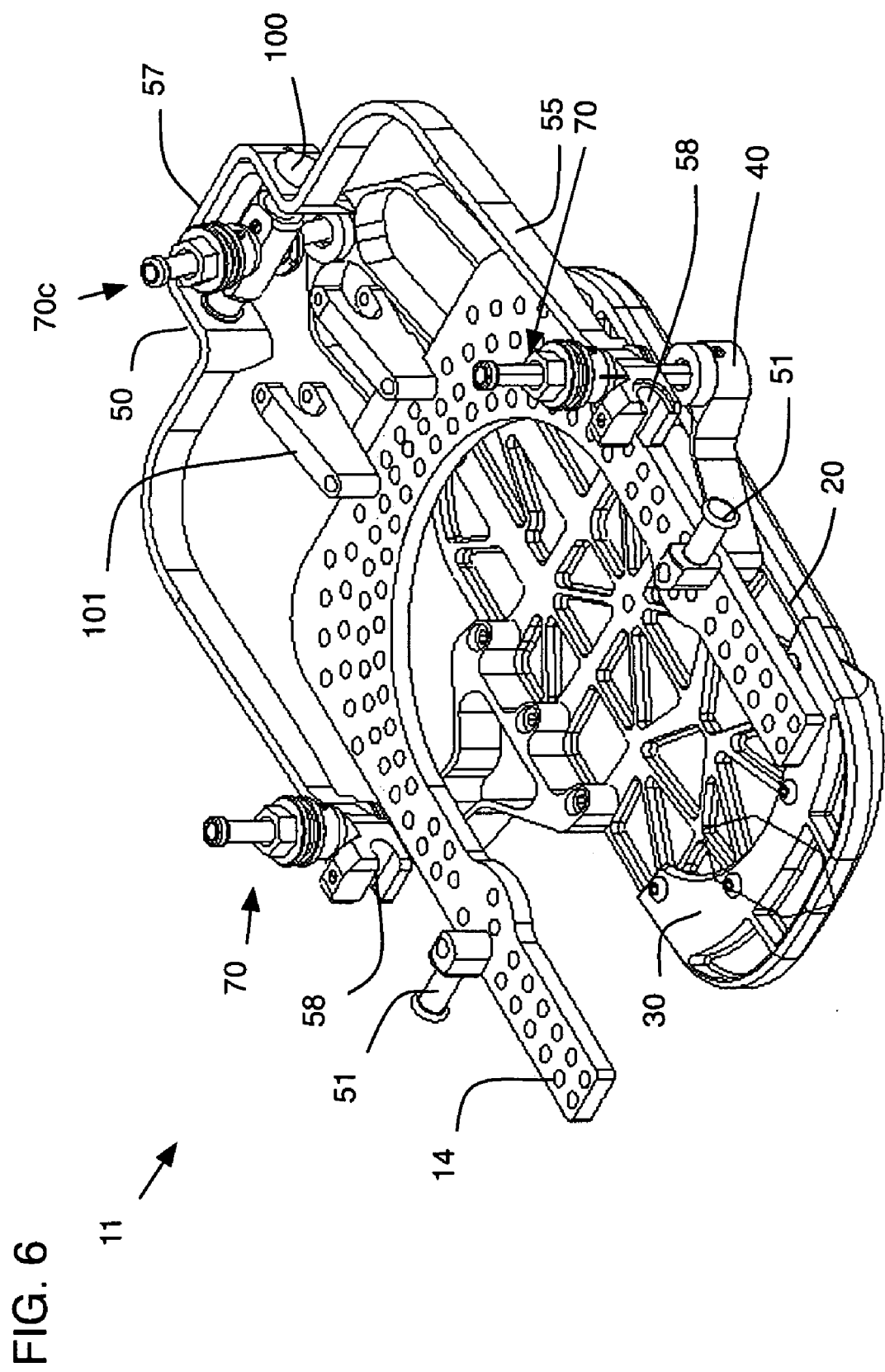
FIG. 6 is an off-set, right-side perspective view of a second preferred embodiment of the present invention.
Figure 7:
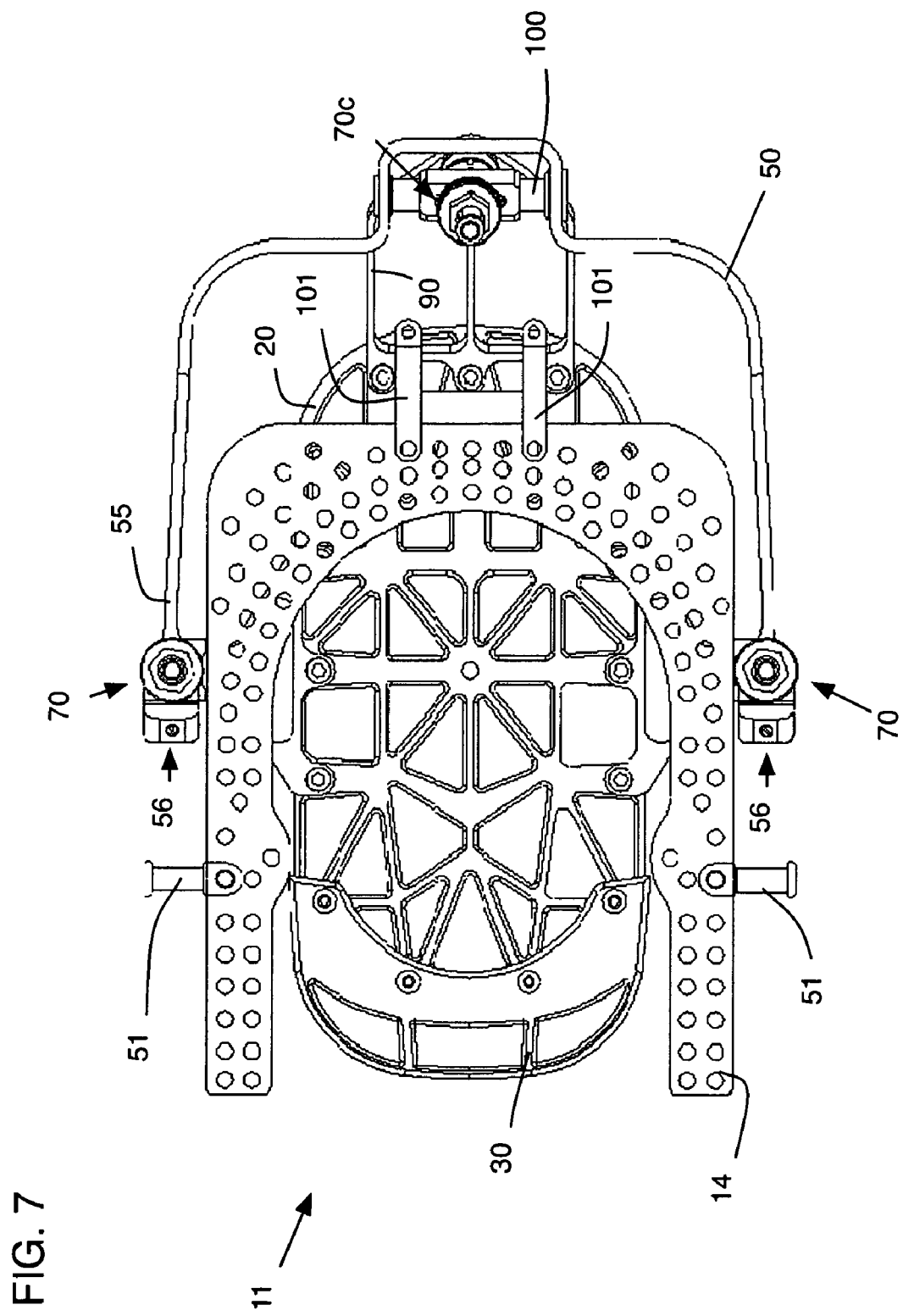
FIG. 7 is a top view of the embodiment of FIG. 6.
Figure 10A:
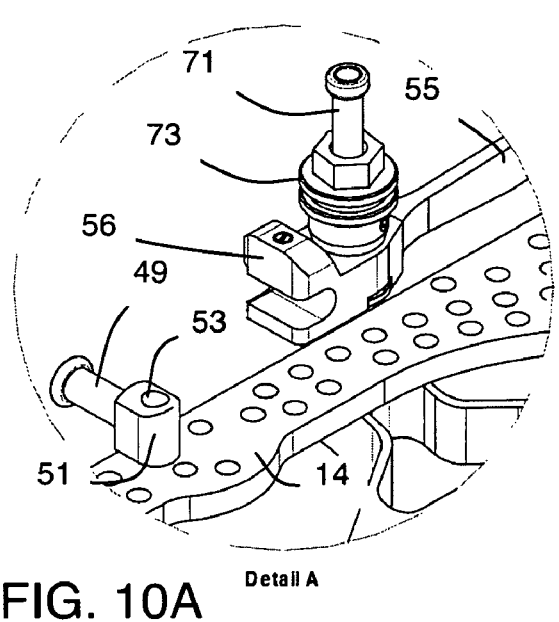
FIG. 10A is a detail view of section "A" of FIG. 10.
Figure 10B:
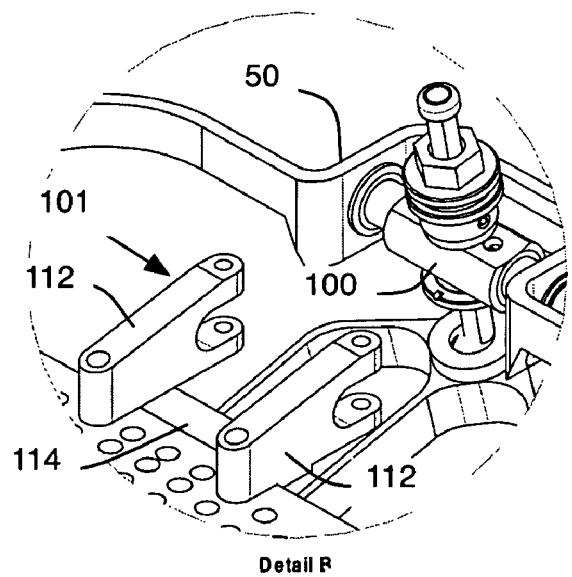
FIG. 10B is a detail view of section "B" of FIG. 10.
Figure 10:
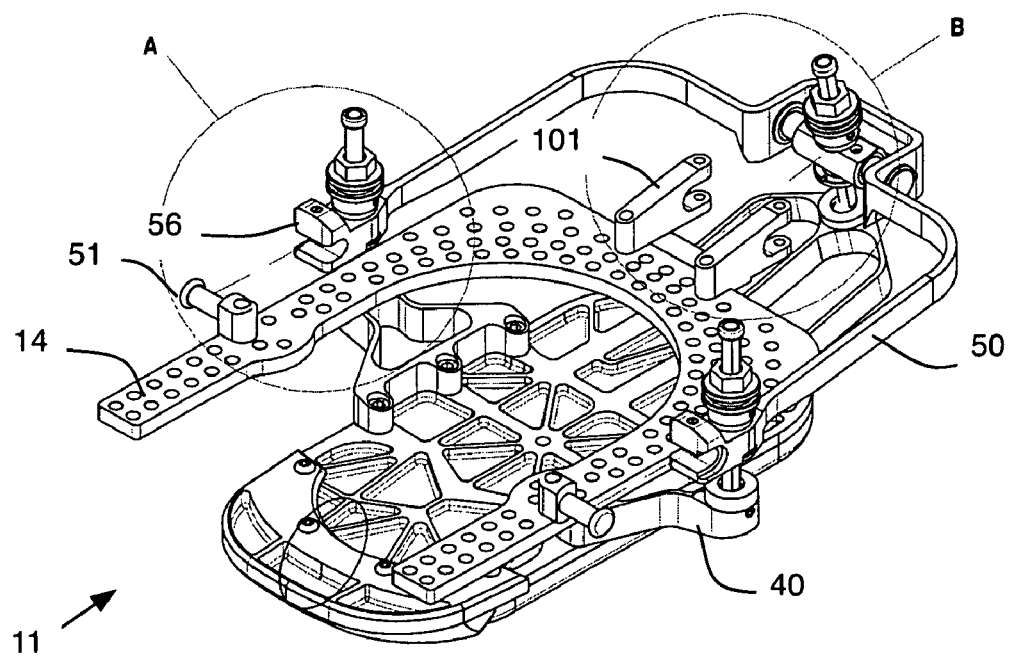
FIG. 10 is an off-set, frontal perspective view of another preferred embodiment of the present invention.
Figure 17:
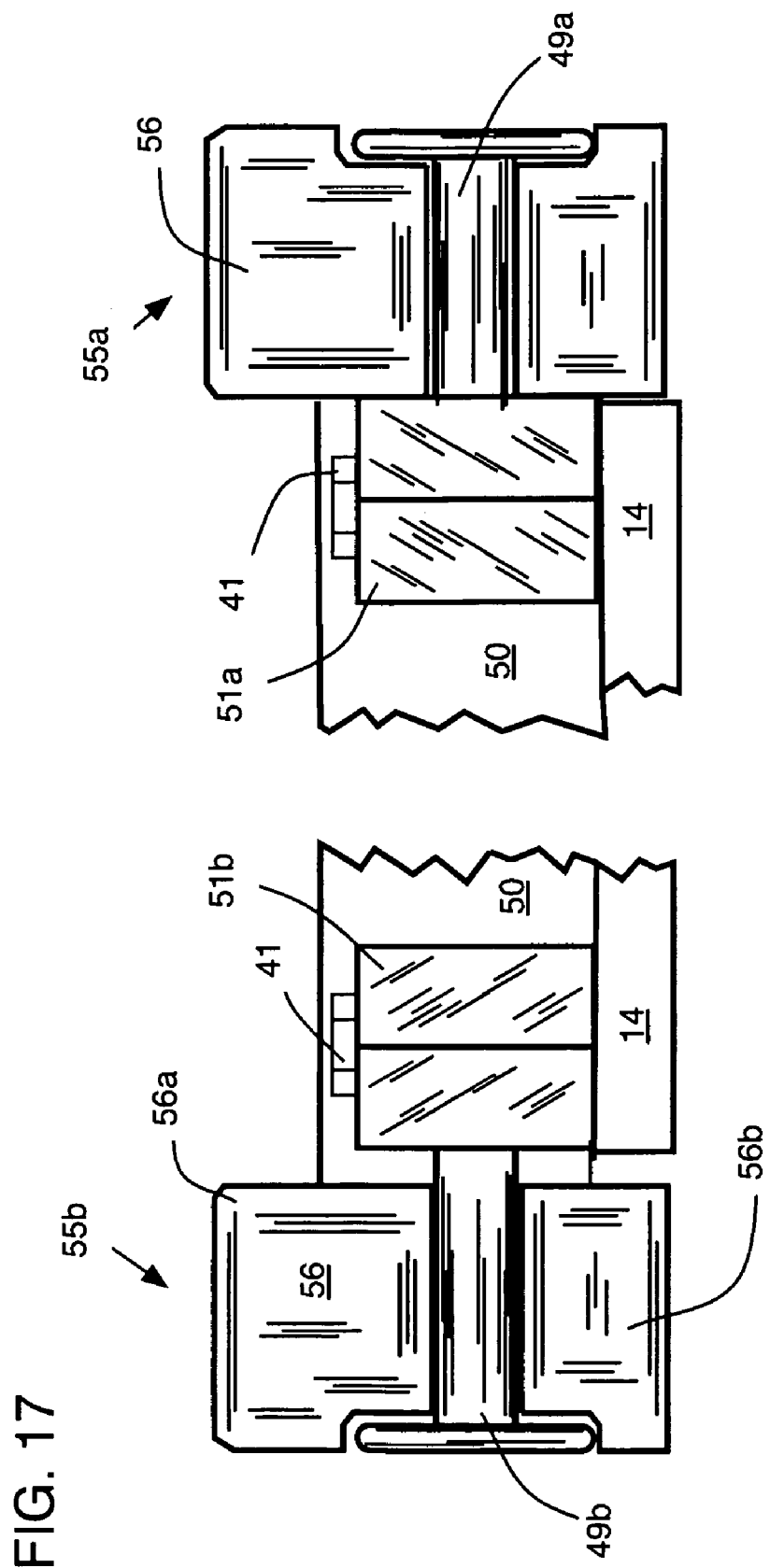
FIG. 17 is a partial detail front fiew of section 17-17 of FIG. 8.

In this first preferred embodiment, a first hinge block 51*a* adapts to couple to the frame by means of known fastening elements, such as set-screws or other similar fasteners depicted generally as item 41 in the drawings. (These hinge blocks 51 are omitted in FIGS. 1-4 are depicted in FIG. 6, for example). Referring specifically to FIG. 17, the first hinge block 51*a* further includes a first hinge-pin 49*a* having a first hinge-pin length, the first hinge pin adapted to selectively and rotably couple to the fulcrum rest 58 at the yoke first arm 55*a* by means of the upper and lower support 56, as generally shown in the figures (and more specifically, 56*a* and 56*b* of FIG. 17). This preferred embodiment further contemplates a second hinge block 51*b* adapted to couple to the frame 14, the second hinge block further comprising a corresponding second hinge-pin 49*b* having a second hinge-pin length, the second hinge pin adapted to selectively and rotably couple to the fulcrum rest 58 at the yoke second arm 55*b* and wherein the second hinge-pin length is greater than the first-hinge pin length thus enabling the yoke to stabilize the base plate laterally relative to the frame, as there is a tight tolerance between the yoke and hinge block on one side of the device and a more loose tolerance on the opposite side—this allows the yoke 50 to flex, yet maintain lateral stability. Additional properties of the yoke 50 are discussed further herein.

Figure 12:
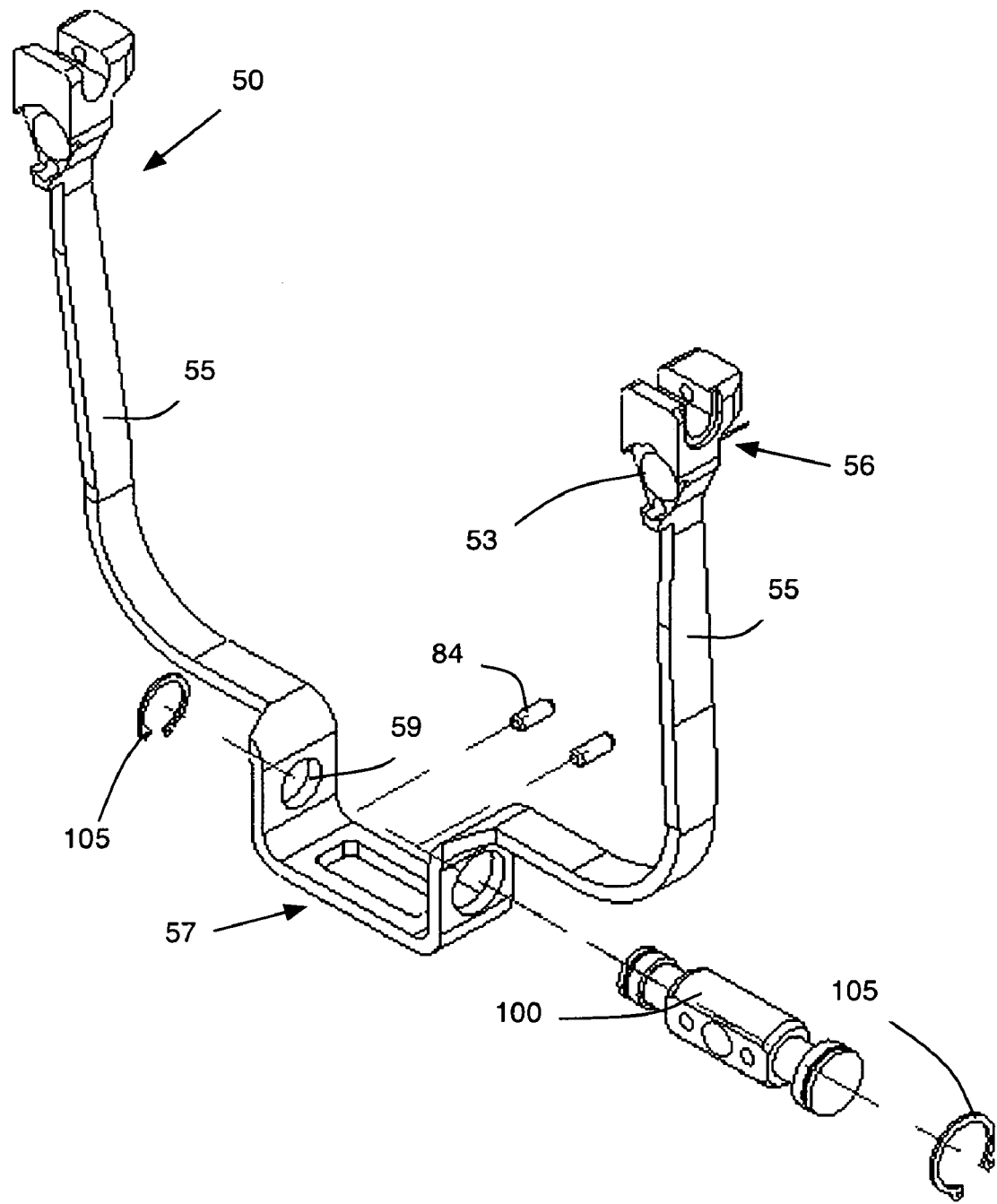
FIG. 12 is an exploded view of other components of the device according to a preferred embodiment of the present invention.

This preferred embodiment further includes a posterior pivot pin 100, as best illustrated in FIGS. 12, 18, and 18A. This pivot pin 100 adapts to rotatably engage the pivot cradle 57 on the yoke 50 and adapts to prevent the yoke from vertical (up and down), fore-aft (horizontal), and left-right (horizontal) displacement at the pivot cradle 57. The pint 100 further includes retaining means, such as a pair of spring-retaining clips 105 to secure the pin in the yoke cradle, yet maintain the ability to rotate. Other elements include a set of bushings 102 and various mounting holes 108 and 106.

This preferred first embodiment further includes a posterior hinge block 101 adapted to couple to the frame 14 at a posterior position by known coupling means, such as the fasteners 41 previously discussed. The hinge block 101 further adapts to pivotably mount to the posterior pivot pin 100. Additionally, the device 10 includes a locking pin 250 adapted to selectively couple the posterior hinge block to posterior pivot pin 100 at hole 106. This locking pin, detailed in FIGS. 18 and 18*a* includes a spring-ball plunger at a distal end of a shaft 256, the shaft being adapted to slideably engage hole 117 on the posterior block and a corresponding hole 108 on the cradle 57. At a proximal end, a release button 252 and grab handle 254 are disposed and work conventionally to release the spring ball plunger at the distal end, thus preventing inadvertent release of the pin when used to lock the yoke 50 to the frame 14.

Additional and optional components contemplated in this first preferred embodiment of the present invention include an air bladder (not shown in the Figures) coupled to a first face of the base plate and adapted for selective volumetric changes and may include a releasably coupling bulb-inflation mechanism for altering the air volume in the bladder according to a patient's comfort needs.

The base plate 20 may additionally include a foam pad (not shown in the Figures) coupled to a top surface by a hook and loop fastening system or by an adhesive.

Figure 5:
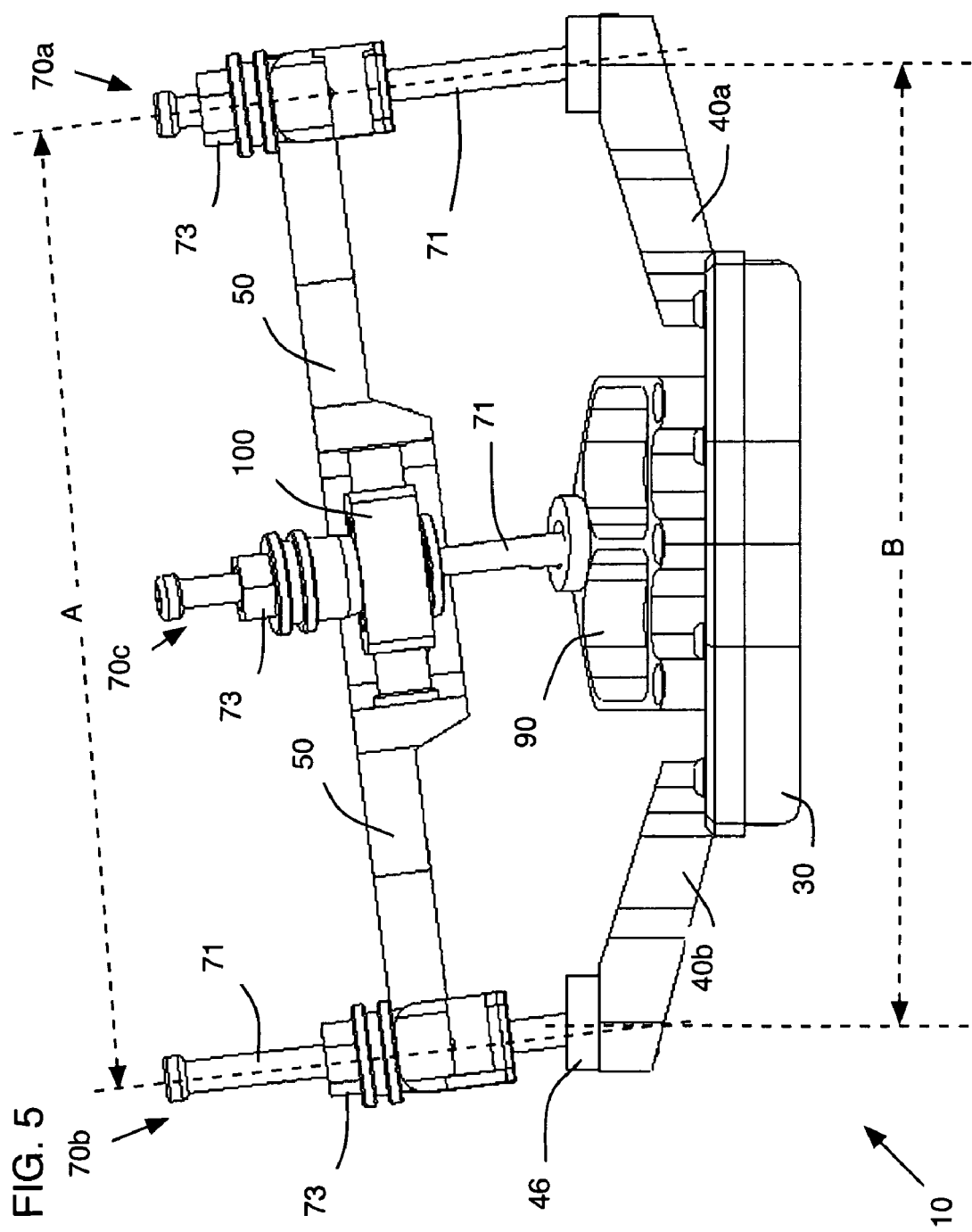
FIG. 5 is a front view of the embodiment of FIG. 1 and illustrates one possible range of adjustment of the base plate.

With reference particularly to FIG. 5, the first preferred embodiment comprising three adjusters enables precise pitch and angulation adjustment of the plane "B" of the base plate relative to a plane A, which represents an external fixation ring (not shown in this FIG. 5). In this view left side medial-lateral adjuster 70*b* is forcing the yoke to an extreme angulation downward vertically and opposite adjuster 70*a* is adjusted to the opposite extreme upward limit of its travel. Yoke 50 ensures that the struts of each respective adjuster remain parallel at the second end and along the longitudinal axis of each respective strut 71. The shoulder 46 containing the ball joint and strut first end enables the strut to pivot to ensure this parallel arrangement of the yoke. Further, as the posterior pivot enables adjustment to the pitch (not perceptible in this FIG. 5), there is a corresponding movement forward or back of each strut. Thus, it is important that each strut pivot in 360-degrees to enable precise positioning of the base plate relative to plane "A" (the external ring).

The present invention, such as the device 10 of FIGS. 1-5, or the system 11 of FIGS. 6-10, for example, recognizes that proper and improved lower extremity fixation requires a precise balance of stability of the components once placed in a pre-set position and flex to enable a more normalized gait during ambulation and, generally, patient comfort during use. In other words, the various components need to provide adjustability, and when adjusted provide stability, yet also provide some flex, give, and/or absorb shock and vibration. All previous prior-art attempts accomplish only stability by providing rigid connectors to the external fixation ring. The present invention, however, incorporates dynamics between cooperating components—namely the three adjusters 70, the yoke 50 and the associated bushings, ball joints and related components as previously presented herein. Thus, using FIG. 5 as a representative example of a pre-determined position of the base plate 20 relative to an external ring 14 or as may be aligned relative to the tibial axis, for example, when viewed from the anterior end, the posterior pivot 100 remains neutral on angulation and needs to pivot from the base plate 20. A shortening occurs on each of the two medial lateral adjusters 70*a* and 70*b*. There is intentional play between the coupling of the respective yoke arms 55*a* 55*b* and the hinge pin 51*a* 51*b* and the inherent spring-like properties of the yoke 50. While there is minimal play between the threads on the associated strut 71*a* 71*b* and threaded sleeve 81 and the relevant bushings, these components resist movement and, thus, provide stability to the entire assembly. In this same position, but when viewed from the side, this apparent shortening is taken up by the posterior adjuster 70*c*, which pivots toward the front of the base plate 20. Importantly, this cooperation of vertically fixed adjusters 70 that can pivot in any direction relative to their respective longitudinal axis combined with the inherent spring-like flex of the yoke 50 and the play enables by the wrists 54, yoke arms 55 and hinge post 51 provides both the stability required for treatment and patient safety as well as the flexibility desired for comfort and shock-absorbtion.

Also, in lieu of the third, posterior adjuster, or in addition to the adjuster, the device 10 optionally includes a pneumatic or hydraulic piston adapted to cushion shock transmitted between the base plate and the external frame.

FIG. 20 illustrates an alternative posterior block 110 consisting of a bridging truss 114 linking two oppositely positioned support members (left and right). Each support member has a corresponding hinge-pin mount cradle 118 consisting of an inverted u-shape surface adapted to engage the posterior pivot pin 100. In FIGS. 1-5, for example, the posterior pivot block is substantially similar, however the mount cradle faces the front of device 10 and is c-shaped instead of inverted u-shaped and facing the bottom of the foot plate as the block 110 in FIG. 20. Accordingly, adjustments are made for the alignment of the locking-pin receiving holes 117. This arrangement enables the patient to more easily step downward into the device 10 when mounting it to an external fixation frame and may prevent unanticipated forward movement in the event the locking pin is not properly seated in position.

Figure 19:
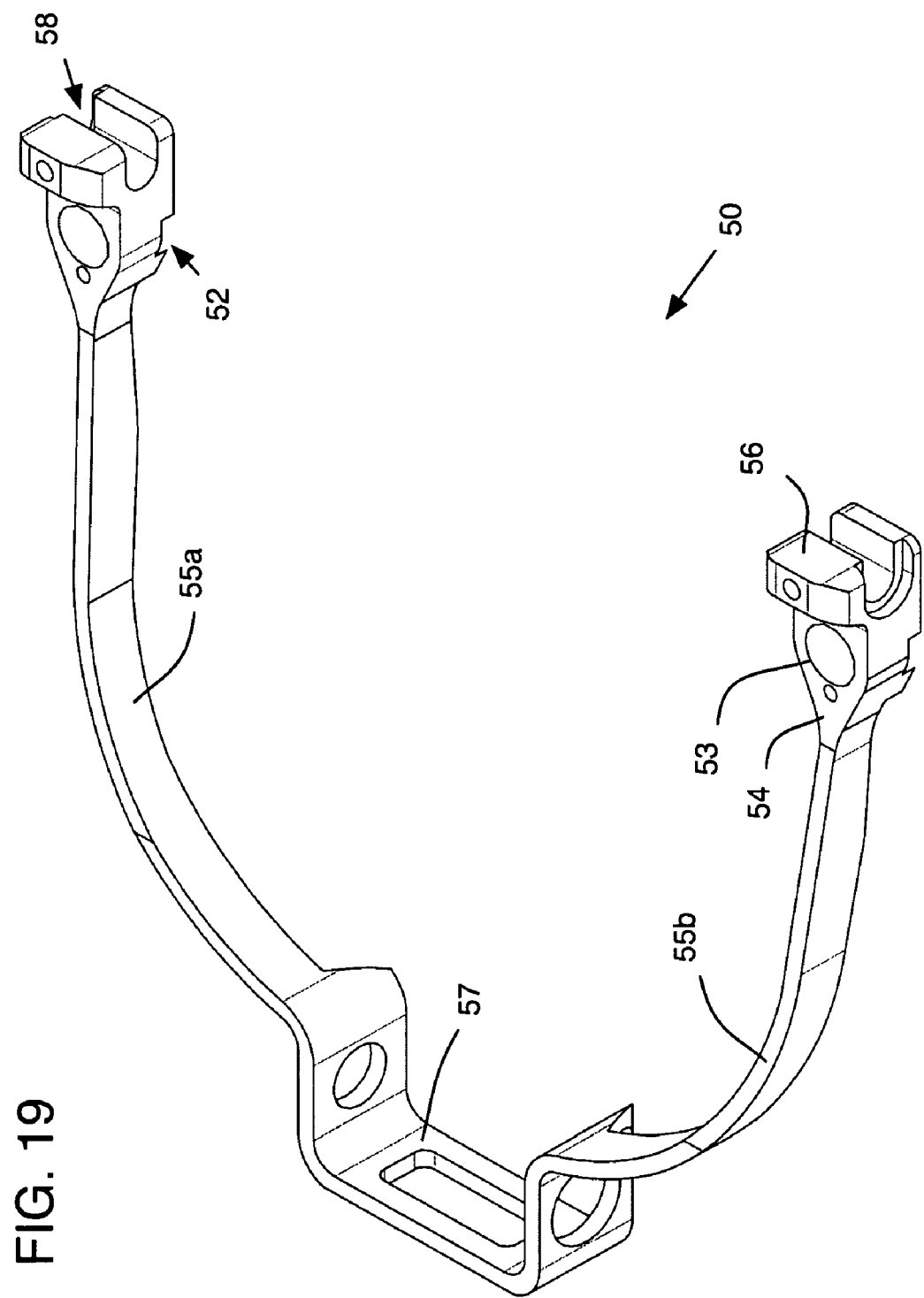
FIG. 19 is an off-set top view of an alternative yoke according to one embodiment of the present invention.

The yoke 50, as depicted in FIGS. 1-4, for example, includes a more square-rounded design. However, a more curve-rounded design, for example as FIG. 19 illustrates, would work equally well. Ultimately, the yoke design may depend on the configuration of the associated frame 14, but can be determined by the care-giver as the circumstances warrant.

A second preferred embodiment according to the present invention contemplates a system 11 for attachment to an external fixation frame as illustrated in FIGS. 5-10. In this system, certain components are carried over from the first preferred embodiment. Where similar components are used, the details previously described are omitted here in the interest of brevity.

The system comprises a first and second hinge block 51 adapted to couple to the frame 14, the first hinge block 51*a* further comprising a first hinge-pin 49*a* having a first hinge-pin length, the first hinge pin adapted to selectively and rotably couple to the fulcrum rest 58 at the yoke first end 56. The second hinge block 51*b*, although similar in appearance and structure as the first hinge block, importantly differs by having a hinge-pin 49*b* having a second hinge-pin length, the second hinge pin adapted to selectively and rotably couple to the fulcrum rest 58 at the yoke second end and wherein the second hinge-pin length is greater than the first-hinge pin length thus enabling the yoke to stabilize the base plate laterally relative to the frame.

This system 11 further includes a posterior hinge block 101 (or alternatively, posterior block 110) coupled to the external fixation frame 14; and an external fixation device 10 of the first preferred embodiment, the device comprising a base plate, a first adjuster 70*a* coupled to the base plate in a fixed vertical position relative to the base plate and being operable to rotate 360-degrees about a longitudinal axis, a second adjuster 70*b* coupled to the base plate 20 in a fixed vertical position relative to the base plate and being operable to rotate 360-degrees about a longitudinal axis, a posterior adjuster 70*c* coupled to the base plate in a fixed vertical position relative to the base plate and being operable to rotate 360-degrees about a longitudinal axis, wherein each respective adjuster 70 enables selective orientation of the base plate 20 relative to the fixation frame 14; and at least one yoke 50 coupled to each the first, second, and posterior adjusters, the yoke further selectively and releasably coupling to each the first hinge pin 51*a*, the second hinge pin 51*b* and the posterior hinge block 101 (or alternatively 110) whereby the external fixation device is operable to be removed from or coupled to the external fixation frame wherein the yoke provides fore-aft and left-right stability of the base plate relative to the fixation frame when the yoke is coupled to each respective first, second, and posterior adjuster.

As FIG. 11 further illustrates, additional spring-ball plungers 84 insert at the end 56 of the yoke arms 55. This provides a more positive engagement of the yoke on the pivot block 51.

Figure 16:
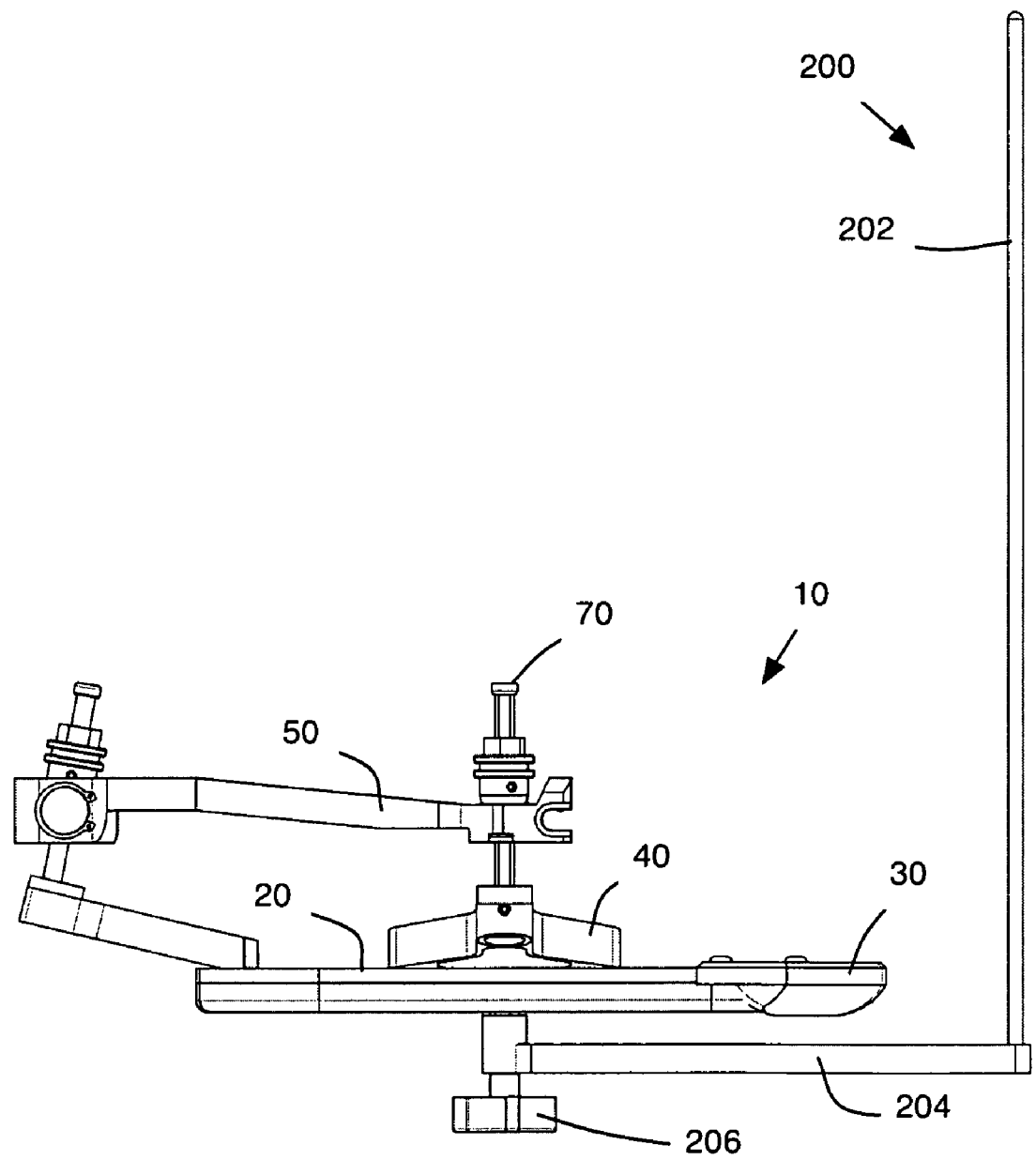
FIG. 16 is a left-side view of an aligning rod according to yet another preferred embodiment of the present invention.

Additionally, the system 11 further contemplates an alignment rod, as FIG. 16 shows. The alignment rod 200 includes a base 204 for providing support means for a vertically arranged alignment guide pin 202. Further, an external fixation device-insertion pin (not shown in FIG. 16) couples to the base 204 on a face opposite from and off-axis with the vertically arranged alignment guide pin 202. Both the insertion pin and the alignment pin are substantially parallel along their corresponding vertical axis. The external fixation device-insertion pin adapted to selectively engage the base plate 20 of the external fixation device 10.

Thus, this alignment guide 200, including the vertical site-guide 202 consisting of an elongated (stainless steel) rod, is well-suited for use to align the device 10 relative to the tibial axis or any other anatomical feature determined suitable by the clinician as deemed necessary based on a particular patient's specific condition, gait, anatomy, treatment regime, and the like. The site-guide 202 enables the doctor or clinician to visually align the site rod 202 parallel to the tibial axis in both an anterior and medial lateral direction. Perpendicularly coupled to the rod 202, the armature (aluminum) 204 adapts to selectively couple to a feature on the bottom of the footplate device 10 by well-understood mounting means such as a threaded attachment knob 206. The armature extends sufficiently to clear the entire footplate, allowing the site rod 360-degrees of rotation around a plane corresponding to the plantar plane of the foot (or parallel to the bottom of the footplate). When the footplate is attached to a patient's foot, the alignment guide more precisely enables a surgeon to adjust the device 10 relative to the tibial axis, for example, or another anatomical feature or axis determined by the clinician. Thus, a treated foot can be dialed in incrementally during the treatment duration so the patient can recover and have improved gait from a repaired (neutral) foot.

On preferred method according to the present invention includes using an external fixation frame 14 and device (of the first preferred embodiment or system of the second preferred embodiment. This preferred method for externally fixating a lower extremity of a patient consists of: providing an external fixation frame having at least one hinge block; providing a external fixation device adapted to removably couple to the external fixation frame by means of the at least one hinge block; providing at least one adjuster having adjustments in multiple planes; and providing a yoke adapted to engage the adjuster and selectively couple to the at least one hinge block.

A second preferred method according to the present invention includes a method for aligning a lower-extremity external fixation device relative to an axis of a tibia. This method comprises: providing an alignment rod comprising a base supporting a vertically arranged alignment guide pin and the base further supporting an insertion pin arranged off axis but substantially parallel to the guide pin; providing an external fixation device comprising at least one adjuster coupled to a base plate, the medial lateral adjuster further being adapted to fixably couple to a yoke and being operable to adjust the position of the yoke relative to the base plate and the base plate further being adapted to receive the insertion pin; inserting the insertion pin into the base plate; and aligning the relative position of the base plate and yoke by visually aligning the guide pin relative to the axis of the tibia and affecting the relative position of the base plate and yoke relative to the axis of the tibia by adjusting each of the at least one adjuster.

FIG. 5 illustrates one possible adjustment position of the device 10 relative to a horizontal plane. A reference horizontal plane typically establishes perpendicular to the tibial axis of the anatomic skeleton. Each adjuster 70 individually adapts to an effective length by incrementing the adjustment knob 73, which requires no tools and simply turns by a hand rotating clockwise to reduce the effective length of the adjuster support strut 71. In this manner the yoke 50 can rotate in three axes. In this view (FIG. 5), the yoke appears off-axis; however, the device 10 couples to known ring-fixation platforms so that the horizontal axis of the yoke is parallel to the horizontal axis of the ring-fixation platform (this is discussed in detail, below). Thus, by adjusting the effective length of the support strut 71 of the respective adjuster or any combination of individual adjusters (of which there are three), any alignment required by the ring-fixation treatment therapy may be achieved. As FIG. 5 shows, the relationship of the support strut 71 relative to the yoke 50 is generally parallel and may be considered axially fixed. However, the bracket end of the support strut 71 includes a ball assembly that enables the strut to rotate in three-axis.

The yoke 50, detailed in FIGS. 11, 12, 17, 18, 18A, and 19 (for example), acts as a flexing suspension member for the device 10. The yoke, a generally C-shaped piece of aluminum (although 2024 aluminum is discussed in a preferred embodiments, those skilled in this art will appreciate that other materials including stainless steel, brass, composites and/or plastics will work equally well), includes a pair of forward-reaching arms 55. Each arm at a first end includes a hinge-block 51, a generally C-shaped coupling block, adapted to engage hinge-post mounted to the frame member 14. The hinge-block 51 further includes a mounting hole 53 disposed generally perpendicular to the coupling axis of the hinge-block 51.

The arrangement of components and the material selection of the components result in device that flexes and provides shock absorbing characteristics when under load. First, the material of the tread-plate includes a type 20-24 alloy of Aluminum, which has inherent resilient characteristics as configured in the present invention. Then enables controlled deflection due to its inherent elasticity. More specifically, the elongated vertically arranged rectangular cross-section of the yoke 50 acts as a tension spring member. It couples to the existing ring frame of the prior art in 3 locations: the left and right medial-lateral support posts, and the posterior adjuster (or more generally adjusters 70). Further, a size difference between the left and right medial-lateral brackets 40 enables the yoke 50 to pivot and flex (preventing binding) relative to the corresponding bracket, which is rigidly coupled to the foot ring of the prior art. This design, further, enables the device 10 to be adjusted in three planes.

All of the adjusters 70 are free at the bottom, (that is, they are fixed in vertical position relative to the base plate but can rotate 360 degrees around their own respective longitudinal axis). But, by fixing the top or intermediate portion of the corresponding strut 71, the cooperation of the three adjusters thereby prevents the yoke from moving like a parallelogram with respect to the base plate. This would make the entire system unstable, or it would require high locking forces to stop them moving like a parallelogram. If you look from the anterior end, the posterior pivot is neutral on angulation and only needs to pivot from the base. From the side, shortening is taken up by the posterior strut. The stable bushing assembly combined with the fact that the posterior strut is limited side-to-side at the top helps keep the assembly stable without being to tight. The adjusters have several key features, 1) the indexing feature holds the position of the knob so that it does not drift during use. This also gives the surgeon feedback for each quarter without having to visually look at the scale for fine adjustments. The strut of the adjuster rides in the bushing to both provide some cushion and to help the assembly turn freely. The knob and strut are assembled so that there is limited axial play, which would make the device 10 feel loose during walking.

FIG. 18 shows a preferred locking pin 250. The locking pin retains the device 10 to the foot ring FR of the prior art. Removing the locking pin enables the device to detach with minimal force, and by hand (no tools) from the foot ring because each support block (two medial lateral blocks and the posterior block) are open on the anterior side (as shown in the various figures). The combination of support blocks support the device from vertical loads, left-to-right, and restrict movement to the posterior, however, anterior movement is restricted solely by the locking pin.

Figure 15:
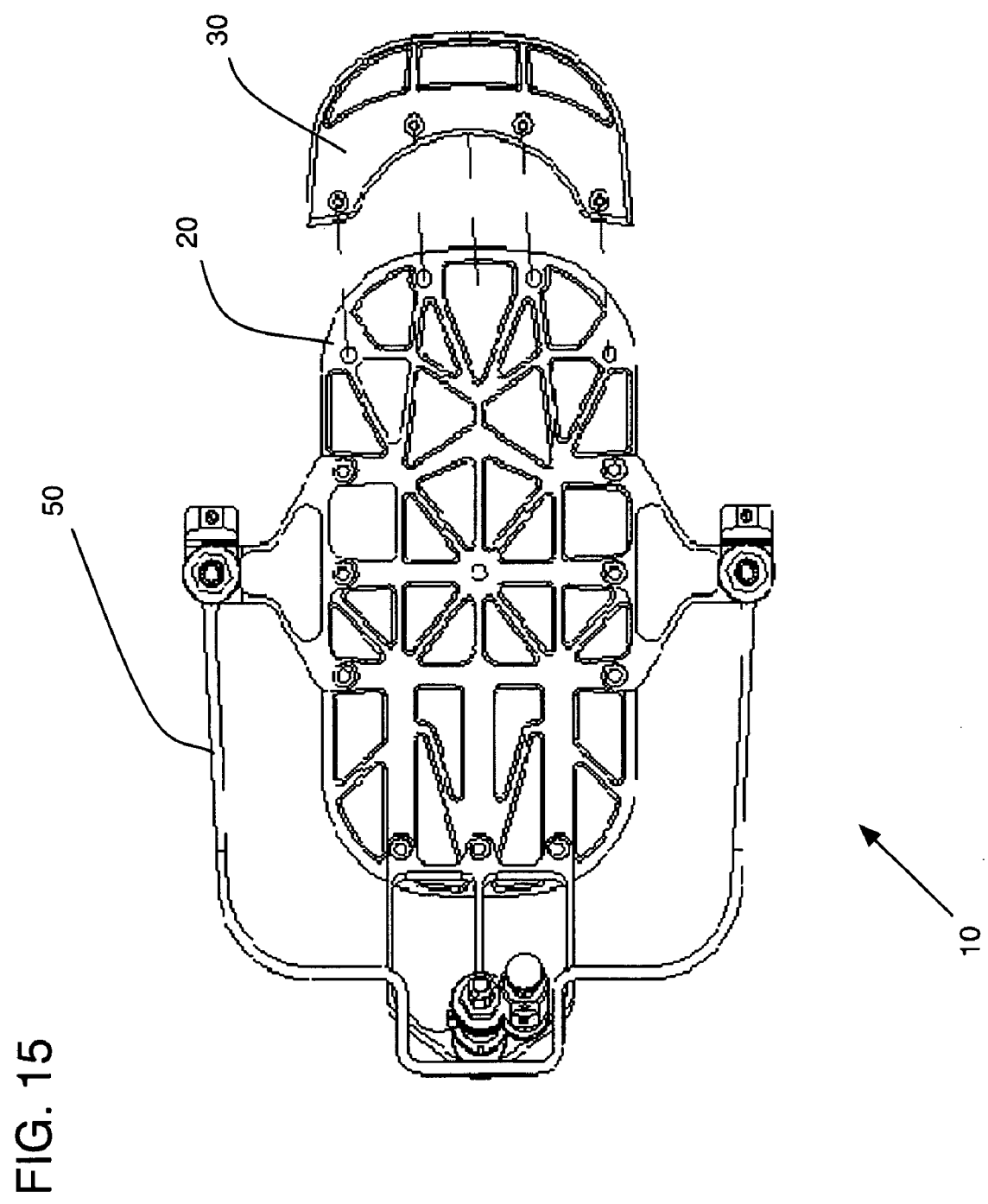
FIG. 15 is an exploded top view of another preferred embodiment illustrating a toe piece in relation to a base of the device of the present invention.

FIG. 15 shows an optional toe-piece 30 adapted to selectively couple to the front end of the device 10. The toe-piece provides additional comfort for the patient. Further, the piece may be fabricated, molded, extruded, formed, forged, etc. from aluminum, stainless, steel, composites, plastics, etc., as would be well-understood in the art.

Although a particular alloy of aluminum is generally contemplated as the preferred material for many of the components of the various preferred embodiments of the present invention, those skilled in the art will appreciate that many other materials are equally suited including, but not limited to, stainless steel, brass, composites, or plastics, for example and may be selected according to a wide variety of criteria including cost, resiliency, durability, weight, ease of manufacturing, economy, among other factors.

Although the invention has been particularly shown and described with reference to certain embodiments, it will be understood by those skilled in the art that various changes in form and detail may be made without departing from the spirit and scope of the invention. And, although claims are not required, we claim at least:

We claim:

1. An external fixation device for attachment to a lower-extremity external fixation frame for a patient, the device comprising:
   a rectilinear base plate adapted to contact a surface during walking;
   at least one adjuster coupled to the base plate, the at least one adjuster comprising a strut having a longitudinal axis defined between a first end and a second, opposite end with an intermediate portion disposed between the first and second ends, and a ball joint adapted to receive the first end of the strut and adapted to enable 360-degrees of rotation of the strut about the longitudinal axis; and
   the base plate further comprising of a first medial-lateral bracket coupled to a first side of the base plate, a second medial-lateral bracket coupled to a second, opposite side of the base plate, and a posterior bracket coupled to the base plate; each respective bracket further comprises a corresponding shoulder offset from the plane of the base plate the shoulder extending upward and away from the base plate along a diagonal defined from about 15 degrees from a horizontal reference plane defined by the base plate to about 45-degrees from the same horizontal reference plane, and wherein each respective bracket adapts to couple to the at least one adjuster and the shoulder adapted to receive the first end of the support strut.

2. The external fixation device of claim 1 wherein the at least one adjuster comprises:
   a first adjuster adapted to couple to the base plate at a first position;
   a second adjuster adapted to couple to the base plate at a second position; and
   a third adjuster adapted to couple to the base plate at a third position.

3. The device of claim 1 wherein:
   the base plate further comprises a substantially flat bottom defining a plane, and a shoulder feature adapted to receive the ball joint of the at least one adjuster whereby the at least one adjuster is pivotably coupled to the base plate to enable the strut to rotate 360-degrees about the longitudinal axis, the longitudinal axis being generally perpendicular to the plane defined by the base plate; and
   a yoke adapted to couple to the at least one adjuster and the yoke further adapted to selectively and releasably couple to the external fixation frame wherein
   the yoke further comprises a generally U-shaped body having a first-yoke arm and a second-yoke arm, each respective yoke arm comprising a wrist feature adapted to enable the strut to pass through a center opening defined by the wrist, a bushing disposed in the wrist feature and adapted to enable slidable engagement of the strut;
   the strut further comprises a threaded body disposed between the first and second end; and
   an adjustment knob assembly adapted to selectively position and rotatably couple on the intermediate portion of the strut whereby rotation in a first direction causes the yoke to move in a corresponding first direction along the strut longitudinal axis and rotation in a second, opposite direction causes the yoke to move in a corresponding second direction along the strut longitudinal axis; and
   whereby the yoke, adjustment knob and strut do not extend below the plane defined by the base plate.

4. The yoke of claim 3 further wherein:
   the yoke-first arm and yoke-second arm further comprises, each respectively, an upper and lower support member defining a generally c-shaped first and second fulcrum rest and a spring-loaded ball plunger arranged perpendicular to the generally c-shaped fulcrum rest, thus enabling the respective first and second yoke arms to selectively couple to the frame; and wherein
   the yoke further comprises a pivot cradle disposed intermediate to the first and second yoke arms.

5. The device of claim 4 further comprising:
   a posterior pivot pin adapted to rotatably engage the pivot cradle and adapted to prevent the yoke from vertical, fore-aft horizontal, and left-right horizontal displacement at the pivot cradle.

6. The device of claim 1 further comprising:
   a posterior hinge block adapted to couple to the frame, the hinge block further adapted to pivotably mount to the posterior pivot pin.

7. The device of claim 1 further comprising:
   a locking pin adapted to selectively couple the posterior hinge block to posterior pivot pin.

8. The device of claim 1 further comprising:
   a first hinge block adapted to couple to the frame, the first hinge block further comprising a first hinge-pin having a first hinge-pin length, the first hinge pin adapted to selectively and rotably couple to the first fulcrum rest at the yoke first arm; and a second hinge block adapted to couple to the frame, the second hinge block further comprising a corresponding second hinge-pin having a second hinge-pin length, the second hinge pin adapted to selectively and rotably couple to the second fulcrum rest at the yoke second arm and wherein the second hinge-pin length is greater than the first-hinge pin length thus enabling the yoke to stabilize the base plate laterally relative to the frame.

9. The device of claim 1 further comprising:
an air bladder coupled to a first face of the base plate and adapted for selective volumetric changes.

10. The device of claim 1 further comprising:
a traction-enhancing surface coupled to a bottom side of the base plate.

11. The device of claim 1 further comprising:
a toe-plate coupled to the base plate.

* * * * *